United States Patent
Roop et al.

(10) Patent No.: US 9,949,632 B2
(45) Date of Patent: Apr. 24, 2018

(54) SURGICAL DEVICES, SYSTEMS AND METHODS

(71) Applicant: Miret Surgical, INC., Elmhurst, IL (US)

(72) Inventors: John Avi Roop, Oak Park, IL (US); Christopher Pell, San Francisco, CA (US); Bryan Duggan, San Francisco, CA (US)

(73) Assignee: Miret Surgical, Inc., Elmhurst, IL (US)

( * ) Notice: Subject to any disclaimer, the term of this patent is extended or adjusted under 35 U.S.C. 154(b) by 40 days.

(21) Appl. No.: 14/770,748

(22) PCT Filed: Mar. 17, 2014

(86) PCT No.: PCT/US2014/030389
§ 371 (c)(1),
(2) Date: Aug. 26, 2015

(87) PCT Pub. No.: WO2014/145595
PCT Pub. Date: Sep. 18, 2014

(65) Prior Publication Data
US 2016/0015253 A1    Jan. 21, 2016

Related U.S. Application Data

(60) Provisional application No. 61/792,957, filed on Mar. 15, 2013.

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00066* (2013.01); *A61B 1/00087* (2013.01);
(Continued)

(58) Field of Classification Search
CPC ............ A61B 1/00087; A61B 1/00098; A61B 1/00131; A61B 1/00133; A61B 1/00135;
(Continued)

(56) References Cited

U.S. PATENT DOCUMENTS 5,547,117 A    8/1996    Hamblin et al.
6,423,075 B1   7/2002    Singh
(Continued)

FOREIGN PATENT DOCUMENTS

WO    2012126967    9/2012

*Primary Examiner* — Ryan Henderson
(74) *Attorney, Agent, or Firm* — Davis, Brown, Koehn, Shors & Roberts, P.C.; Sean D. Solberg

(57) ABSTRACT

Devices, systems and methods for abdominal surgery is disclosed. The system can have a scope coupled to an introducer. The system can have one or more end effectors that can be attached to the introducer and inserted into the abdomen through a small puncture through the patient's umbilicus. The end effector can have a surgical tool, such as a grasper. The system can have a manipulatable control arm that can be inserted into the abdomen through a small puncture through the patient's body wall. The end effector can be attached to the control arm and simultaneously or concurrently detached from the introducer or tray. The control arm can then manipulate the end effector to perform the surgery.

20 Claims, 42 Drawing Sheets

(51) Int. Cl.
| | |
|---|---|
| *A61B 17/00* | (2006.01) |
| *A61B 17/28* | (2006.01) |
| *A61B 17/29* | (2006.01) |
| *A61B 17/34* | (2006.01) |
| *A61B 17/128* | (2006.01) |
| *A61B 1/04* | (2006.01) |
| *A61B 90/00* | (2016.01) |

(52) U.S. Cl.
CPC ...... *A61B 1/00096* (2013.01); *A61B 1/00098* (2013.01); *A61B 1/042* (2013.01); *A61B 1/313* (2013.01); *A61B 17/1285* (2013.01); *A61B 17/29* (2013.01); *A61B 17/3417* (2013.01); *A61B 17/3423* (2013.01); *A61B 90/361* (2016.02); *A61B 2017/00473* (2013.01); *A61B 2017/347* (2013.01); *A61B 2017/3445* (2013.01); *A61B 2017/3447* (2013.01)

(58) Field of Classification Search
CPC ....... A61B 1/00154; A61B 1/01; A61B 1/012; A61B 1/18; A61B 1/042; A61B 1/313; A61B 1/3132; A61B 1/3135; A61B 1/317; A61B 1/32; A61B 17/00; A61B 17/28; A61B 17/29; A61B 17/34
USPC ....... 600/104, 106, 107, 114, 170, 171, 173, 600/174, 204
See application file for complete search history.

(56) References Cited

U.S. PATENT DOCUMENTS

| | | | |
|---|---|---|---|
| 6,440,061 B1* | 8/2002 | Wenner | A61B 1/3132 600/114 |
| 6,527,704 B1 | 3/2003 | Chang et al. | |
| 2001/0018553 A1* | 8/2001 | Krattiger | A61B 1/00183 600/173 |
| 2002/0049367 A1 | 4/2002 | Irion et al. | |
| 2003/0055437 A1 | 3/2003 | Yasunaga | |
| 2003/0130559 A1 | 7/2003 | Morin et al. | |
| 2004/0044363 A1 | 3/2004 | Fowler | |
| 2005/0245942 A1 | 11/2005 | Dipoto | |
| 2008/0287926 A1 | 11/2008 | Nabil | |
| 2011/0144659 A1 | 6/2011 | Sholev | |
| 2011/0208007 A1* | 8/2011 | Shohat | A61B 17/3403 600/227 |
| 2011/0245844 A1* | 10/2011 | Jinno | A61B 34/37 606/130 |
| 2011/0288536 A1* | 11/2011 | Dejima | A61B 17/29 606/1 |
| 2012/0083826 A1 | 4/2012 | Chao et al. | |
| 2014/0275779 A1* | 9/2014 | Ma | A61B 1/008 600/109 |

\* cited by examiner

SURGICAL DEVICES, SYSTEMS AND METHODS

CROSS REFERENCE TO RELATED APPLICATIONS

This application claims priority from U.S. Provisional Application 61/792,957, filed Mar. 15, 2013, and entitled "Surgical Device and Method," which is hereby incorporated herein by reference in its entirety.

TECHNICAL FIELD

The disclosed surgical devices, systems, and methods relate generally to performing surgery, e.g., laparoscopic surgery, and more particularly, to laparoscopic surgical tools and to systems and methods including such tools.

BACKGROUND

Surgery has become increasingly less invasive thanks to advances in medical technology. Laparoscopy is the dominant minimally invasive surgical (MIS) approach used today and has replaced many traditional "open" approaches.

Minimally Invasive Surgery (MIS) offers several advantages compared to open surgical procedures including minimal trauma to the abdominal wall and hence less postoperative pain, fewer wound complications, earlier patient mobilization, and shorter length of stay. Laparoscopic access to the peritoneal space is the dominant MIS approach when performing minimally invasive abdominal operations.

Recent clinical studies show that further reduction of the size and/or number of incisions may offer added benefits such as faster recovery, less pain, reduced operative time, and improved cosmetic result. Such benefits may have physical and psychological impact. However, the size of the tool tips on conventional instruments used in laparoscopic procedures generally limit the ability to reduce the size of the incisions and trocars needed for such procedures.

Single-port surgery involves a multi-channel port that is typically placed in the belly button. This results in a hidden post-operative scar. Through these channels, standard laparoscopic tools can be inserted. However, manipulation is more challenging because the tight aperture of the belly button and strong connective tissue in the abdominal wall forces all the instruments to move dependent on one another. In addition, the surgeon's hands are crowded together because of these constraints. Triangulation is largely lost. This makes the procedure frustrating and often more time consuming to perform compared to other approaches.

A number of commercially available tools have been designed to circumvent some of these limitations. Some are variations of standard laparoscopic instruments but have articulating toolheads. Such designs are intended for re-enabling triangulation. However, constraints of the belly button port may force these articulating tools to cross, thus reversing the left-right motion between what the surgeon does with his hands and what he sees on the video monitor. Also, the complex mechanics behind the articulation may drive the cost up significantly.

There is a need in the art for improved laparoscopic tools and techniques.

SUMMARY

Figure 1:
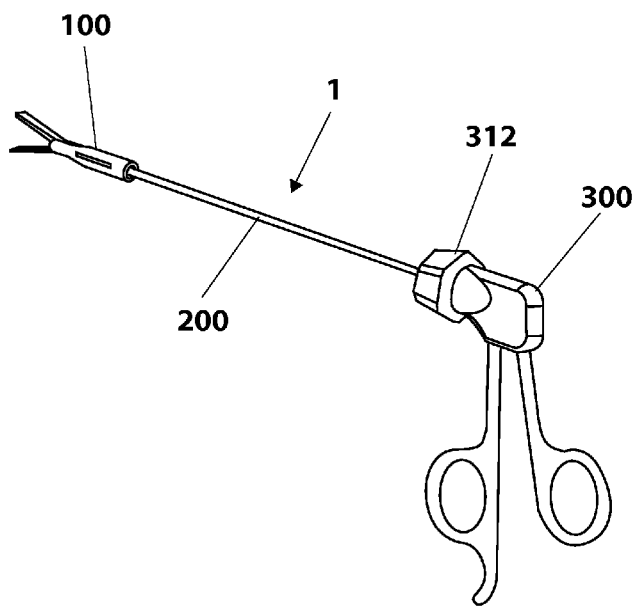
FIG. 1 is a perspective view of one embodiment of a surgical device.

The disclosed surgical device is directed to apparatus, systems, and methods for performing surgery, e.g., laparoscopic surgery. More particularly, the disclosed surgical device is directed to laparoscopic surgical tools and to systems and methods including such tools, e.g., designed to facilitate surgery while minimizing the number and/or size of access sites used and/or minimizing visible scars.

The present disclosure relates to methods and equipment necessary to perform an elective surgical procedure to remove the gall bladder (Laparoscopic Cholecystectomy) with no visible scarring to the patient. The systems, methods and devices described here achieve a no-scar result by using detachable instruments that result in only a needle point puncture through the abdomen.

DETAILED DESCRIPTION

The various systems and devices disclosed herein relate to devices for use in medical procedures and systems. More specifically, various embodiments relate to various medical devices, including laparoscopic and endoscopic devices and related methods and systems.

It is understood that the various embodiments of the disclosed devices and related methods and systems disclosed herein can be incorporated into or used with any other known medical devices, systems, and methods.

For example, the various embodiments disclosed herein may be incorporated into or used with any of the medical devices and systems disclosed in copending international Applications WO 2010/114634 A1, published on 7 Oct. 2010 and entitled "SUrgical Device And Method," and WO 2012/112622 A2, published on 23 Aug. 2012 and entitled "Apparatus, Systems, and Methods for Performing Laparoscopic Surgery," both of which are hereby incorporated herein by reference in their entireties.

Certain device and system implementations disclosed in the applications listed above can be positioned into a body cavity of a patient in combination with a support component similar to those disclosed herein.

Existing scar-free options are often complex, frustrating and time consuming for surgeons. These disadvantages limit the user base of surgeons as most surgeons are not willing to sacrifice time, potential complications and frustration. Therefore, for a scar-free surgical system to be successful, ease-of-use must be addressed.

As described elsewhere in our previous applications, a modular system that attaches a standard sized toolhead to a narrow shafted handleset across the abdominal wall at any desired point can preserve the triangulation and visualization surgeons are used to and because the toolhead is of a standard size, the manipulations and forces available to the surgeon are comparable. In summation, once the tools are built the surgeon can proceed like a standard laparoscopic procedure. This means that the only non-standard parts of the procedure are the toolhead attachment and/or removal process and addressing more complex procedure that require specialized tools. A principle aspect of the present disclosure relates to making these processes and tools as easy to use as possible Improving the user experience can be done through the simple addition of haptic and or visual indicators to make the current state of the tool readily apparent to the operator and help eliminate uncertainty in the assembly or operational steps.

Further, making the system more durable and easier to clean will make it more suitable for a wider range of procedures and facility ecosystems, alleviating concern from the user.

By adding simple and ergonomic controls to the handleset used to properly align the internal attachment features can help the surgeon more quickly and effectively maintain the proper positioning of the handle during attachment/detachment.

Introducing the toolhead with the laparoscopic device (also referred to herein as a "scope") through a single port eliminates the need for a second port, further reducing the number of ports required and freeing up the surgical space near the scope insertion point. By providing an introduction tool that holds the toolhead and the laparoscopic device in a controlled manner the proper visualization and positioning can be provided with minimal effort on the surgeon.

Complex procedures require specialized tools. One of the most commonly required complex tools is a clip applier to provide ligation. Due to the limitations in toolhead size associated with a modular system, certain clips cannot be provided in the standard laparoscopic way so alternative means must be offered to provide the surgeon with the tools they need. Accordingly, the presently disclosed systems, methods and apparatus aim to provide substantial improvements to the art.

Turing to the figures in detail, FIGS. 1-32D illustrate exemplary embodiments of various laparoscopic and endoscopic surgical devices and instruments. In endoscopic and laparoscopic surgical procedures, a trocar is used to puncture the patient's body in order to provide an access port through the abdominal wall to allow for the introduction of surgical instruments. A typical trocar requires a one centimeter incision. Typically, a first trocar is placed above the umbilicus to introduce a camera to allow the surgeons to view the surgical site. The camera view is projected on a screen outside the body, which the surgeon and his or her assistants watch in order to appropriately manipulate the instruments inside the body cavity. Additional trocars are used to introduce surgical instruments, such as grasping tools, scissors, clips, and electrosurgical instruments. Typically, the laparoscopic instruments extend toward the surgical target from either side of the video camera. This "triangulation" of the instruments provides the most ergonomic and intuitive set up for the surgeon.

The disclosed surgical devices relate to laparoscopic surgical tools designed to not leave a visible scar. These laparoscopic surgical tools generally comprise two categories, handle tools and laparoscopic devices (or "scopes"). Handle tools are comprised of a handle, a trans abdominal drive system and a toolhead/tip. The trans abdominal drive system is intended to transmit motion, energy, and/or data across a patient's body cavity wall without leaving a permanent scar. The trans abdominal drive system can be applied to laparoscopic surgical procedures including but not limited to appendix removal, gall bladder removal, hernia repair and uterus removal. Current laparoscopic tools require a port or trocar to be placed across the patient's body cavity wall. Said ports or trocars are large and leave a scar. The trans abdominal drive portion of the laparoscopic tool allows the surgeon to use laparoscopic tools across a body cavity wall without leaving a scar.

A modular surgical instrument that enables standard laparoscopic techniques through small puncture holes in the body wall and methods of using the same are disclosed. The assembled modular instrument has a handle, a small diameter needle-like cannular shaft (e.g., less than or equal to about 2.5 mm diameter), and a toolhead. The toolhead is initially inserted through a trocar port at a separate location (such as the umbilicus). This step relies on a secondary introducer device. The cannular shaft unit is actually two coaxial shafts that move relative to one another. It is pierced through the body wall into the body cavity. The cannular shaft attaches to the toolhead inside the body. The handle is attached to the external part of the cannular shaft. This step can be done before or after insertion of the cannular shaft into the body cavity. The toolhead or end effector is the attached to the cannular shaft and removed from the introducer tool. Once the modular instrument is fully assembled, the toolhead is manipulatable through the puncture hole at any desired site. There is a coaxial locking mechanism between the cannular shaft and the toolhead that locks both the external shaft and the internal "active" shaft. The locking mechanism utilizes a series of channels and keyways so that the tool tip is fully constrained to the cannular shaft with redundant locking for toolhead retention. The toolhead can only be unlocked from the cannular shaft using a complementary/corresponding component attached to an introducer or remover device tool. The toolhead may have a variety of forms and functions, selected by the operator specifically for the task relevant to the procedure. The mechanisms used to drive the toolhead may be simple mechanical (e.g., through coaxial movement), powered (e.g., torquing power drill), energized (e.g., electrocautery), pneumatized (e.g., vacuum suction), or combinations thereof.

The disclosed devices, systems and methods relate to improved surgical devices, systems and methods which relate to improvements relating to both handleset tools 1 (such as that in FIG. 1) and scopes 2 (discussed in relation to FIGS. 11A-B and 17A-23F). FIG. 1 depicts an exemplary embodiment of a handle device 1 comprising an end effector 100, a cannula or control shaft 200 and a handleset 300. Introduction of the cannula 200 into the abdomen is well-established in the art. The distal end of the cannula adjacent to the handleset can have a twist control knob 312. Rotating the twist control knob 312 can calibrate and/or attach and lock, or detach and unlock the end effector 100 from the control shaft 200 (e.g., and concurrently attach and lock the end effector 100), and/or rotate the tool 100 during use. In certain embodiments, the handleset 300 is in operational communication with the cannula 200 and end effector 100 so as to actuate the end effector, as described elsewhere herein.

Figure 2:
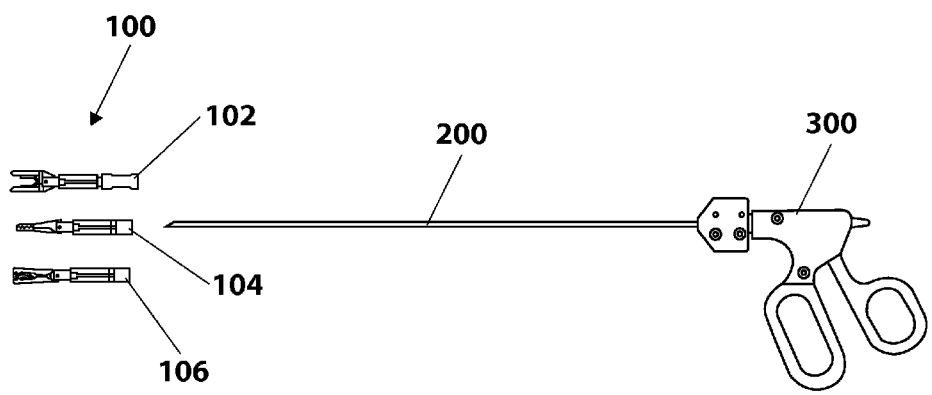
FIG. 2 is a side view of another embodiment of device surgical device showing multiple possible end effectors.

As shown in FIG. 2, exemplary embodiments of one aspect of the system comprise a handle tool device further comprising an end effector 100, a cannula shaft 200, and handleset 300. An exemplary embodiment of a surgical device showing multiple optional end effectors 100 is depicted in FIG. 2. FIG. 2 depicts the various end effectors 100, including (from top to bottom) a metal clip applier 102, a grasper 104, and a hemo-lock clip applier 106, each of which may be fitted as the end effector 100 depending on the configuration desired.

Figure 3A:
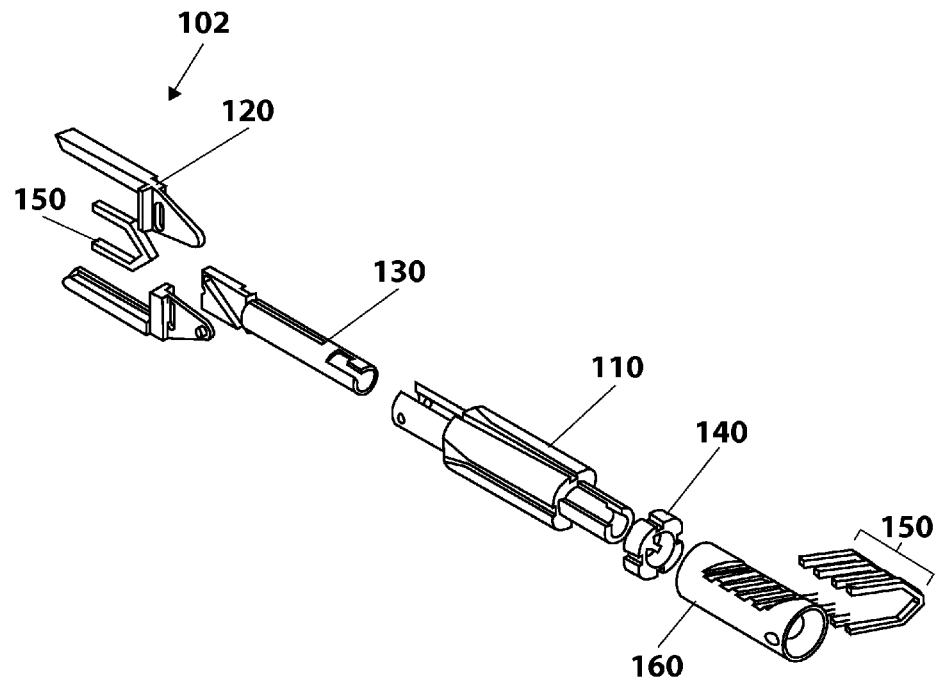
FIG. 3A is a perspective exploded view of a clip applier end effector comprising a plurality of deformable clips according to one embodiment.

FIG. 3A shows an exploded view of an exemplary embodiment of one aspect of a surgical device comprising a clip applier end effector assembly 102. In this implementation, the clip applier 102 comprises a housing 110, a plurality of deformable clips 150 (use of which is described further herein in relation to FIGS. 24A-25E), a cannula guide cap further having a clip rack 160, a clip applier jaw 120, an actuating link 130, and a locking ring 140.

Figure 3B:
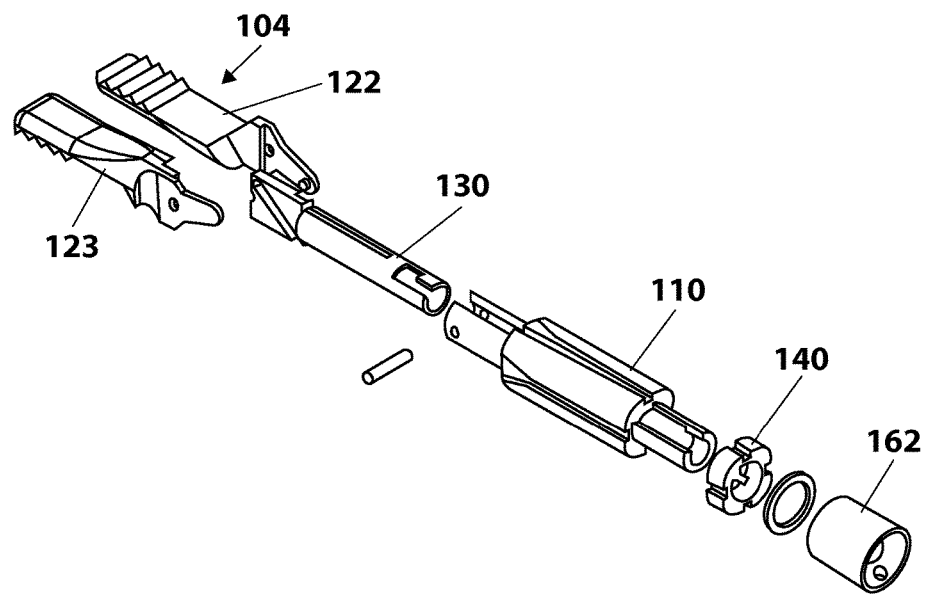
FIG. 3B is a perspective exploded view of a grasper end effector according to one embodiment.

Various embodiments of the surgical device grasper end effector assembly 104 are represented in FIG. 3B. In these embodiments, the surgical device comprises an integral housing 110, an actuating link 130, a locking ring 140, first and second grasper jaws 122, 123, and a cannula guide cap 162. In certain embodiments, and as shown in FIGS. 3B-3C, a mounting pin is also provided for connection of the housing and jaws 122 and 123 such that they can pivot around the pin.

Figure 3C:
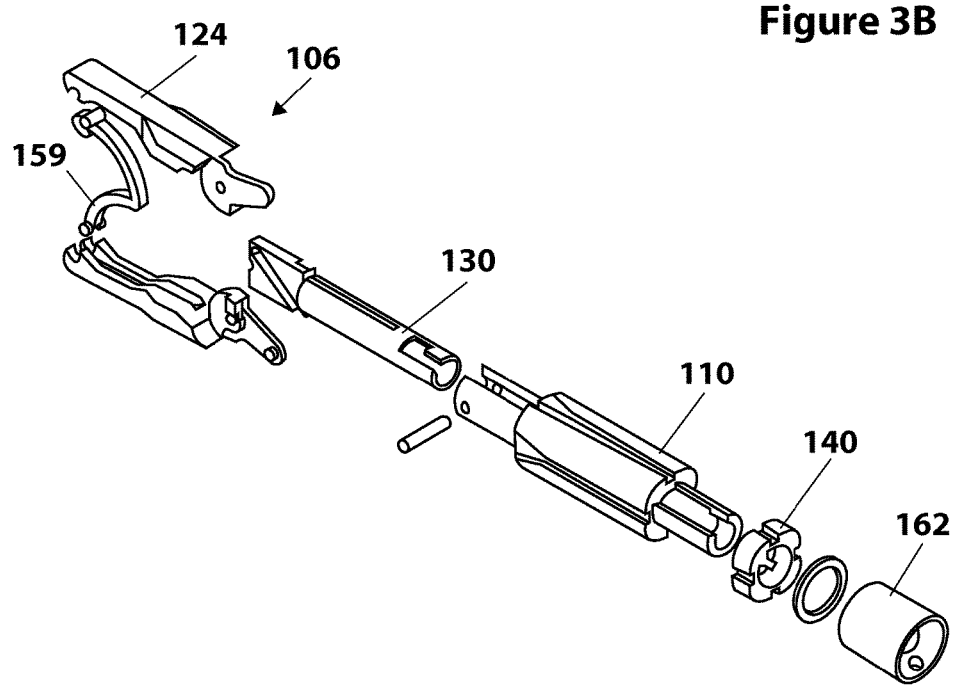
FIG. 3C is a perspective exploded view of a hemo-lock jaw end effector according to one embodiment.

FIG. 3C shows various embodiments of the surgical device in an exploded view of the hemo-lock end effector assembly 106, use of which is described in detail herein in relation to FIGS. 30A-32D). In these embodiments, the surgical device comprises an integral housing 110, an actuating link 130, a locking ring 140, a cannula guide cap 162. This embodiment further comprises a hemo-lock jaw 124 and a hemo-lock clip 159.

Figure 4A:
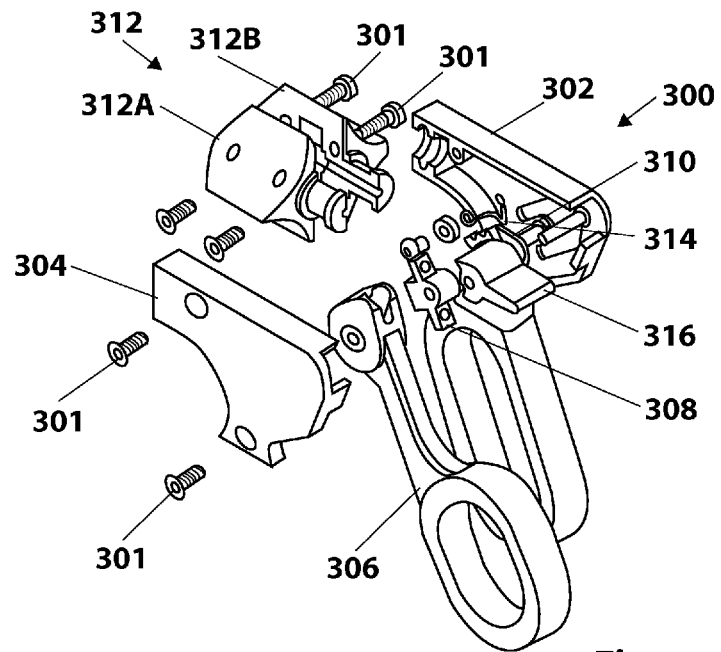
FIG. 4A is an exploded perspective view of one embodiment of the handle of a device.
Figure 4B:
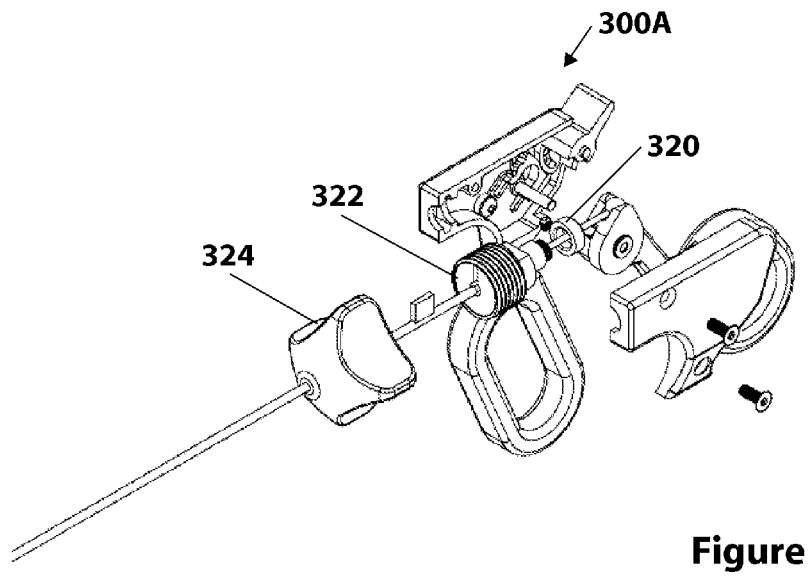
FIG. 4B is an exploded perspective view of an alternate embodiment of the handle of a device.

FIG. 4A depicts an exploded view of an exemplary implementation of the handleset 300. In this embodiment, the surgical device further comprises a distal handle 302, a distal handle cover 304, a proximal handle 306, a proximal handle adjuster 308, a locking slide 310, a rotation knob 312, a detent spring 314, and a toggle switch 316. In these embodiments, a plurality of threaded fasteners 301 may be utilized to couple the distal handle 302 cover so as to partially surround the proximal handle 306 and rotation knob 312. In further embodiments, the rotation knob 312 also comprises multiple rotation knob portions 312A, 312B, coupled by one or more threaded fasteners 301. FIG. 4B depicts an alternate embodiment of the handleset 300A, comprising an O-ring retainer 320 a threaded proximal rotation knob 322 and internally threaded distal rotation knob 324.

Exemplary embodiments of the surgical device and system comprise various tactile and visual systems to provide additional user stimuli and improve insertion. FIG. 5A-5E illustrate exemplary embodiments of the surgical device and system having improvements to the insertion of the control shaft—shown in this embodiment as a cannula 200—into the end effector 100 for the surgical device. In certain prior art embodiments, alignment of the cannula 200 with the end effector could be difficult and cumbersome. In these exemplary embodiments, user frustration can be reduced by using visual and tactile indicators. In the embodiment shown in FIG. 5A, a colored stripe 202 is used to clearly indicate to a user that the locking components are in the proper position and orientation. Such visual and tactile indicators can be used independently or in conjunction with each other. As is apparent to one of skill in the art, various embodiments are possible.

Figure 5A:
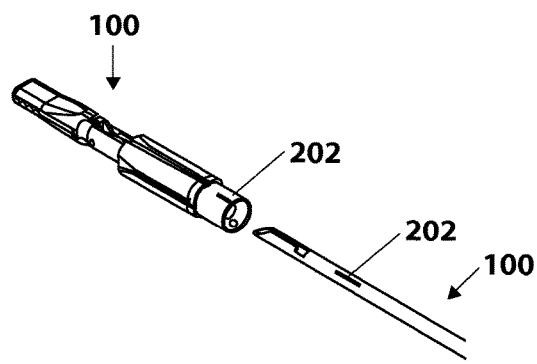
FIG. 5A is a perspective view of a cannula being inserted into an end effector, wherein the cannula has a visual indicator for assisting insertion, according to one embodiment.
Figure 5B:
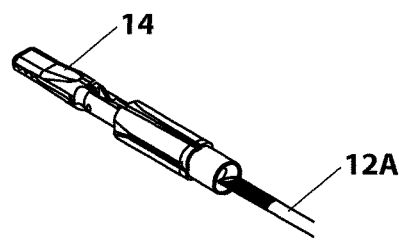
FIG. 5B is a perspective view of a cannula being inserted into an end effector, wherein the cannula has a visual indicator for assisting insertion, according to one embodiment.
Figure 5C:
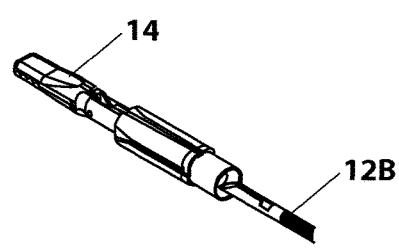
FIG. 5C is a perspective view of a cannula being inserted into an end effector, wherein the cannula has a visual indicator for assisting insertion, according to one embodiment.
Figure 5D:
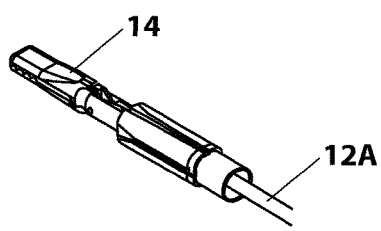
FIG. 5D is a perspective view of a cannula being inserted into an end effector, wherein the cannula has a visual indicator for assisting insertion, according to one embodiment.
Figure 5E:
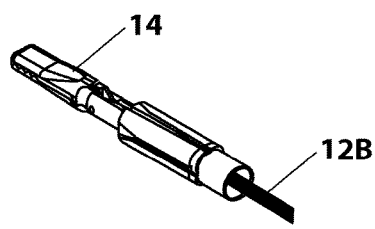
FIG. 5E is a perspective view of a cannula being inserted into an end effector, wherein the cannula has a visual indicator for assisting insertion, according to one embodiment.

FIGS. 5B-5E depict further embodiments of the use of visual indicators in the surgical device. In exemplary embodiments, the tip of the outer cannula shaft can be colored using paint, chemical or laser etching, annodization, or printing to create a colored section of the shaft that is only visible when the shaft is not fully seated in the end effector 14. FIG. 5B depicts a colored cannula tip 12A, prior to insertion into the end effector. FIG. 5D depicts the colored cannula tip having been fully inserted into the end effector 14. In another exemplary embodiment, the entire outer cannula shaft can be colored or covered leaving the tip of the cannula shaft exposed as the base material. When the outer cannula needle is fully seated in the end effector, the exposed material is no longer visible. This coloring could be created using other functional components of the cannula assembly such as the insulation necessary for cautery applications. FIG. 5C depicts an exemplary embodiment comprising a colored cannula needle 12B prior to insertion into the end effector 14, while FIG. 5E depicts the colored cannular needle 12B following insertion.

Figure 6:
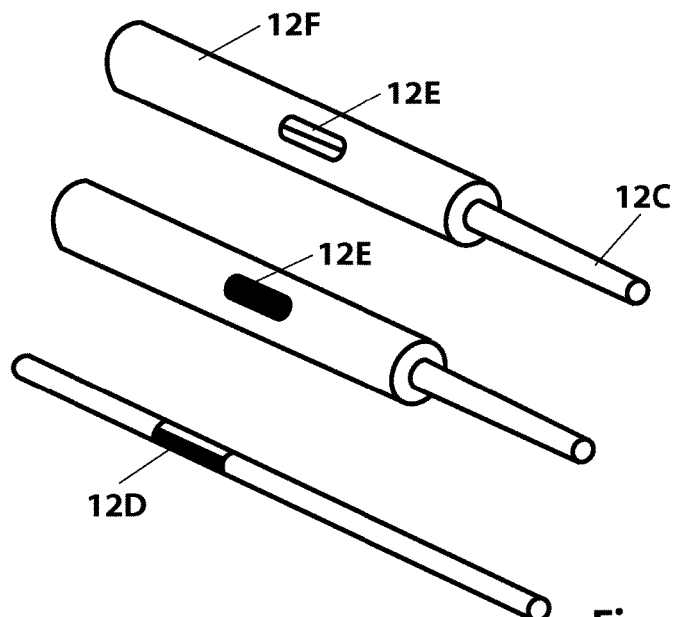
FIG. 6 depicts various perspective views of embodiments of a surgical device comprising a cannula locking mechanism further having a visual indicator.

In further exemplary embodiments of the surgical device—as depicted in FIG. 6—a locking mechanism is utilized to place the surgical device into a "locked state." This "locked state" may be utilized to convey to users of the surgical device that the inner cannula shaft 12C is correctly positioned relative to the outer cannula shaft 12F. In these embodiments, the end effector 14 (not shown) further comprises a locking ring 140 which rotates the inner cannula shaft 12C to engage an actuating link 130 (not shown). The only components that rotate during the locking action are the inner cannula shaft and locking ring (not pictured), so there are many locations where their orientation relative to the other components can be exploited to create a visual indicator. By adding alignment markings 12D to the inner cannula shaft and creating cutouts 12E on the outer cannula shaft, in these embodiments, the relative rotation exposes distinct markings on the inner cannula shaft 12C. By way of example, the inner cannula shaft can have adjacent colored regions 12D with different colors such as red to represent "unlocked" and green to represent "locked." In certain embodiments, the locking ring is rotated to the locked position it reveals the green indicator and the red indicator when it is unlocked. In other exemplary embodiments, additional indication components can be attached to the inner or outer cannula. In alternate embodiments, the rotation between the inner and outer shaft components and proper orientation can be signaled to a user by way of a variety of devices, wherein said rotation can drive levers, turn wheels, or provide tactile or other feedback to the user with devices such as detents, create audible sounds, activate magnetic sensors, and other devices that could be used to signal that the inner shaft has been rotated to the correct position to begin tool operation.

Figure 7A:
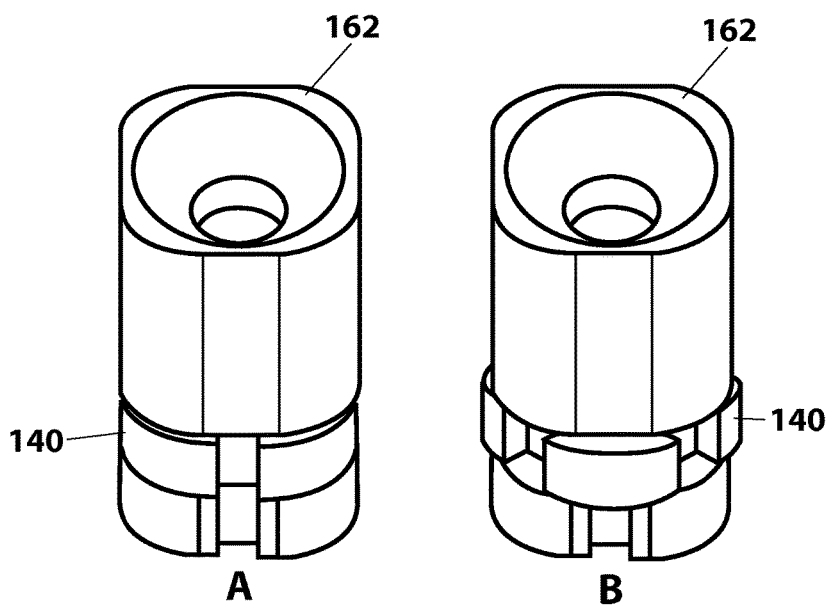
FIG. 7A depicts a perspective front view of a cannula guide cap having a locking ring, according to one embodiment.
Figure 7B:
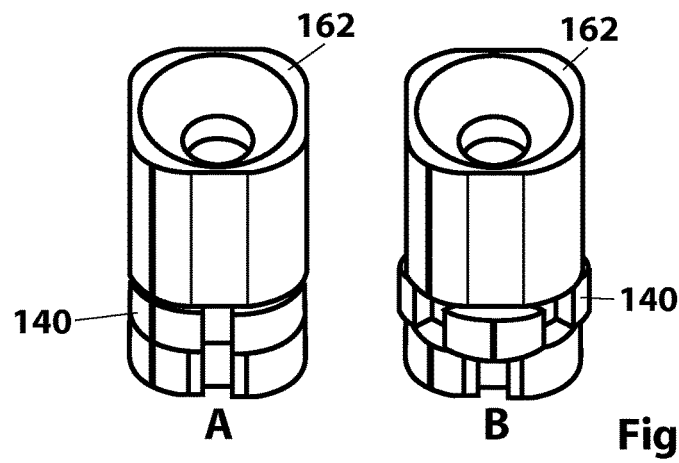
FIG. 7B depicts a perspective front view of a cannula guide cap having a locking ring and visual indicator, according to one embodiment.
Figure 7C:
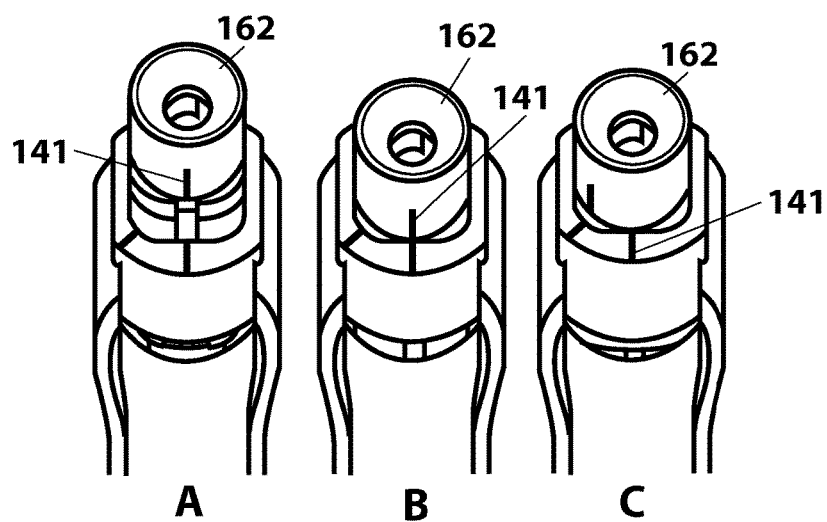
FIG. 7C depicts a perspective front view of a cannula guide cap having a locking ring and visual indicator, according to an alternative embodiment.
Figure 7D:
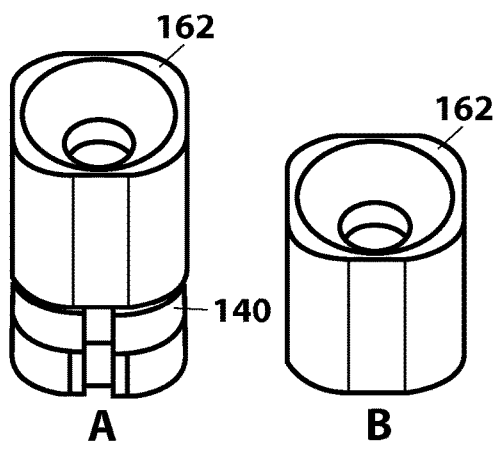
FIG. 7D depicts a front perspective view of the surgical device showing a colored locking ring, not fully inserted and fully inserted, according to an exemplary embodiment.

In certain exemplary embodiments, the rotational position of a locking ring 140 communicates to the user the inner and outer cannula components are properly aligned, certain exemplary embodiments of which are depicted in FIG. 7A-7D. FIG. 7A depicts an implementation showing locked (A) and unlocked (B) positions for the locking ring 140 and the cannula guide cap 162. FIG. 7B depicts an implementation showing an alignment line to show locking ring 140 position in locked (A) and unlocked (B) implementations. FIG. 7C depicts an implementation showing alignment line 141 on the introduction device in the unseated (A), seated (B) and seated and locked (C) positions for the locking ring 140. FIG. 7D depicts an implementation showing a colored locking ring 140, not fully inserted (A) and fully inserted (B). As such, in certain implementations, the rotation of the locking ring 140 relative to the integral housing and guide cap 162 is used as a visual indicator of rotation.

In further embodiments, the faces of the locking ring are colored or otherwise marked so as to be readily apparent to a user. In such embodiments, if the ring is in the unlocked state, the colored ring face is visible to the user. If the ring is in the locked position, the guide cap and integral housing act to cover the colored faces, thus obscuring the unlocked indication from view. A further embodiment comprises alignment marks 141 festooned to the locking ring so as to align with accompanying marks on the integral housing and/or the guide cap. When the marks 141 are aligned, the user is made aware that the end effector is locked to the cannula assembly.

Because the times when knowledge of the relative alignment between the locking ring and integral housing or endcap correspond to the moments when the end effector is either being inserted or removed from the introduction device, the view of the locking ring 140 may be partially or completely blocked. To address this, a visual indicator 141 for the locking ring can be replaced by an indicator on the introduction device. In certain implementations, a certain number of possible orientations are given for the end effector in the introduction device. As is shown in FIG. 7C, by placing an identical number of visual indicators on the end effector and one or more on the introduction device, a user may be assured that at least one indicator combination can be used to assess the alignment of the locking ring 140 relative to the integral housing and or the guide cap 162.

Figure 8A:
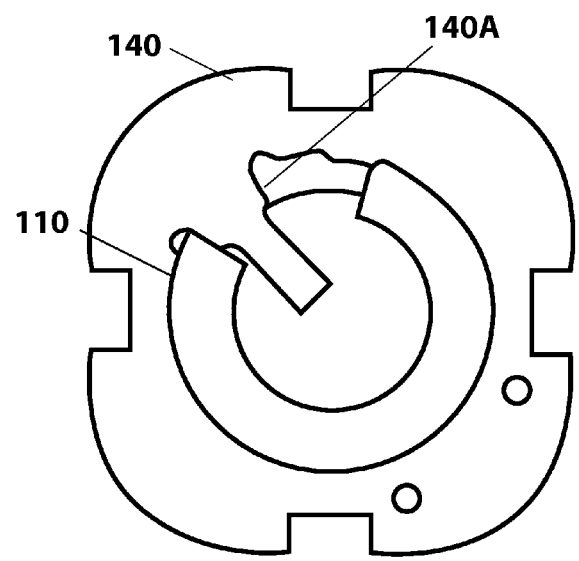
FIG. 8A depicts a cross-sectional view of the locking ring further comprising an integral detent in operational communication with the end effector integral housing, as is depicted elsewhere in relation to FIGS. 3A-3B.

FIG. 8A depicts a side view of the locking ring 140 further comprising an integral detent 140A in operational communication with the end effector integral housing 110, as is depicted elsewhere in relation to FIGS. 3A-3B. In certain embodiments, user feedback can be enhanced and the locking mechanism further secured with the addition of a detent mechanism between the locking ring and the end effector assembly. The addition of an integral detent 140A provides a further tactile indicator for a user when locking the end effector assembly to the cannula shaft. It also increases the amount of force required to rotate the locking ring, making it more difficult for incidental contact with the locking ring to unlock the end effector assembly, thereby preventing "drift," or other unintentional rotation.

Because the rotational position of the inner shaft is matched to that of the locking ring 140 the same outcome could be achieved by placing a detent feature between the inner and outer shafts such that when the end effector is engaged by the shafts and is rotated the detent feature "snaps" into place. Placement of the integral detent between the shafts also allows placement of the mechanism in the handle set, which may provide additional manufacturing space. The same detent could also be used to hold the shafts rotationally in the "unlocked" position which could reduce the time used to align the shafts when inserting the shafts into the end effector. In further or alternative embodiments the detent 140A could be replaced by a frictional element such as an O-ring. This would accomplish the "drift" prevention aspects by increasing the force needed to displace the shaft position but may not provide the same haptic feedback to the user.

Prior implementations of the surgical device locking mechanism converted linear motion between the inner and outer cannula shafts into rotational motion of the end effectors. However, certain embodiments of the locking mechanism of the current system involves transferring rotational motion in the inner shaft to an end effector or other device requiring rotational motion such as a rotational cutting tool. As shown in FIG. 8A, these embodiments of the locking mechanism are similar to the locking mechanism embodiments previously described herein, having a locking ring 140, or outer shaft that can be engaged to end effector via rotation or other described means. Because the rotation—rather than the linear position—of the inner shaft is being transmitted, the coupling between the inner shaft and the working tool may be engaged. By way of example, and described elsewhere herein, in certain embodiments the surgical device further comprises a clutch mechanism that translates the rotation from the face of a rotating shaft to that of another shaft that is connected to the end effector.

Figure 8B:
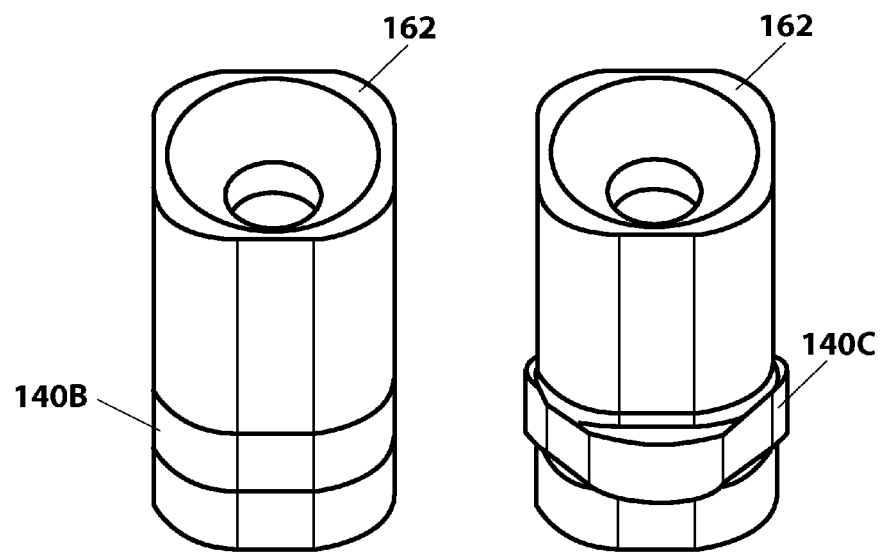
FIG. 8B depicts a further front perspective view of the surgical device further comprising a slot free design, according to certain implementations.

In certain implementations, the surgical device further comprises a slot free design, as is depicted in FIG. 8B. In these implementations, the interface between the locking ring 140 and the cannula guide cap 162 comprises a non-cylindrical locking ring 140B so as to create an overlap 140C between the locking ring 140B and the corresponding feature on the introduction device with the other components in the end effector assembly. In these embodiments, when the end effector is secured in the introduction device, the end effector is rotated to make it impossible for the end effector to slide out of the introduction device. When the end effector is rotated in the introduction device, the surfaces inside the introduction device align with the surfaces on the end effector to allow the end effector to move freely. In the latest prototype components, this can easily be accomplished with the substantially rectangular locking ring having rounded corners. In other embodiments other non-cylindrical shapes can be employed, as would be apparent to one of skill in the art.

Figure 9A:
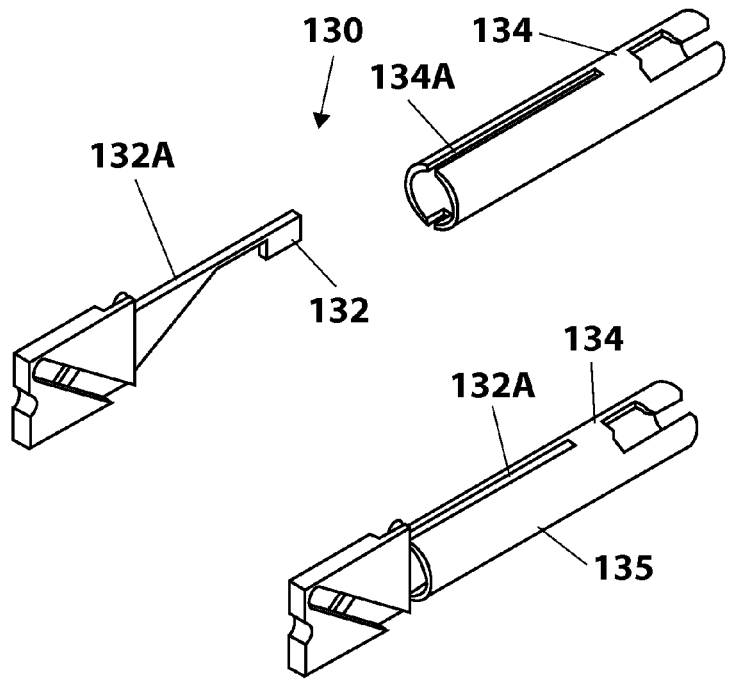
FIG. 9A depicts various exploded views of various embodiments and implementations of the surgical device which address improvements to the drive mechanism.
Figure 9B:
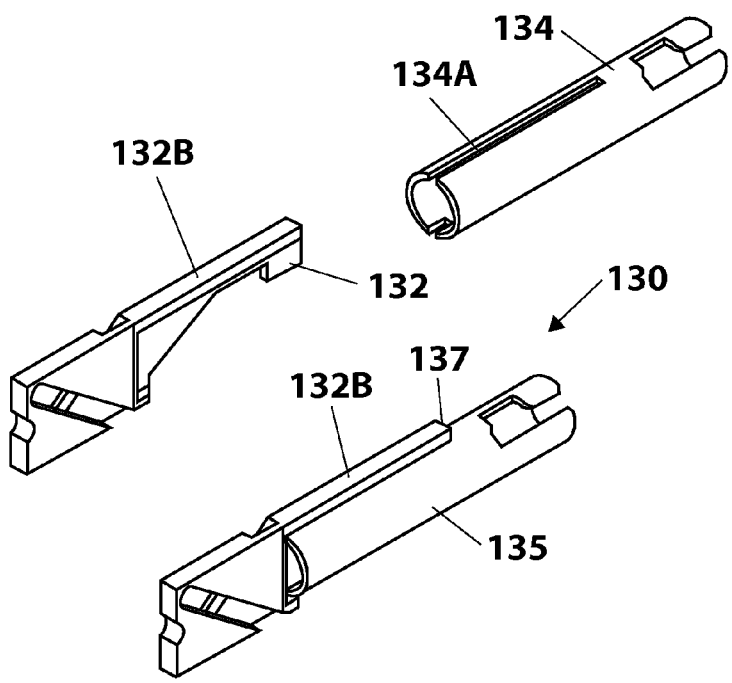
FIG. 9B depicts various exploded views of various embodiments and implementations of the surgical device which address improvements to the drive mechanism.
Figure 9C:
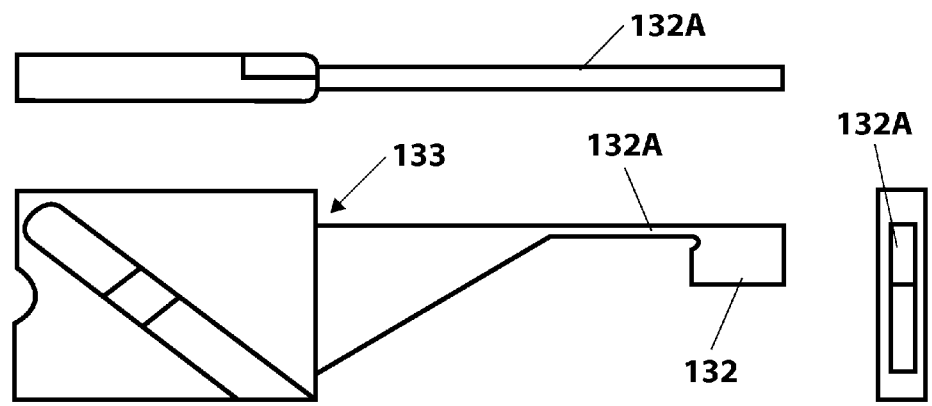
FIG. 9C depicts various exploded views of various embodiments and implementations of the surgical device which address improvements to the drive mechanism.

FIGS. 9A-9C depict exploded views of various embodiments and implementations of the surgical device which address improvements to the drive mechanism 130. To address problems with stress failure in the actuating link observed in prior art devices, exemplary embodiments of the surgical device comprise an actuating link tooth 132 with an extended spine 132A that is welded into a hypodermic tube 134 that has a slot 134A that fits the spine. The tube 134 and tooth are welded together (as shown by 135) along the length of the spine 132A. As shown in FIG. 9A, in certain embodiments, the material used along the spine 132A is extremely thin and the available weld area is limited. By raising and increasing the thickness of the external spinal portion (132B) the spine is structurally more robust and the available weld area is increased, as is depicted at 137 in FIG. 9B. These embodiments require altering the actuating link such that deep channels 134 are made to correspond to the raised and thickened spine. As a byproduct of this the spine 132 of the actuating link and the channel 134 of the actuating link begin to act as additional rotational alignment features for the actuating link, as would be apparent to one of skill in the art. In the embodiment of FIG. 9C, as with FIG. 9A, the extended spine 132A is recessed 133, such that it is configured to fit into the hypodermic tube by way of a "keyhole" configuration, as is known in the art.

Figure 9D:
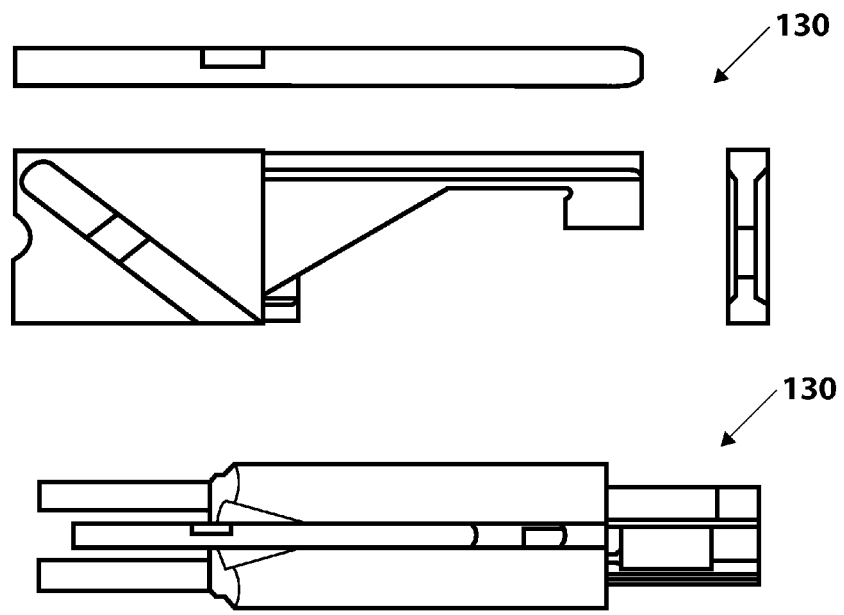
FIG. 9D shows an implementation of the surgical device comprising a non-tubular actuating link design.

FIG. 9D shows an implementation of the surgical device comprising a non-tubular actuating link 130 design. In these embodiments, the actuating link tube is eliminated. Eliminating the actuating link tube greatly reduces the manufacturing effort required to make the actuating link because aligning and welding the actuating link is no longer be required. Additionally, the inner diameter of the integral housing can then be reduced to correspond to the outer diameter of the cannula needle. Reduction of the inner diameter of the integral housing allows for a reduction of the outer integral housing dimensions without compromising the material thickness.

Figure 10A:
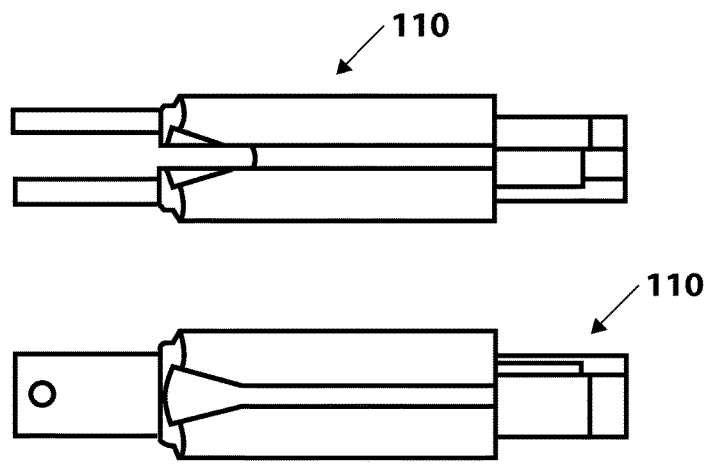
FIG. 10A depicts top and side views of a prior art surgical device.
Figure 10B:
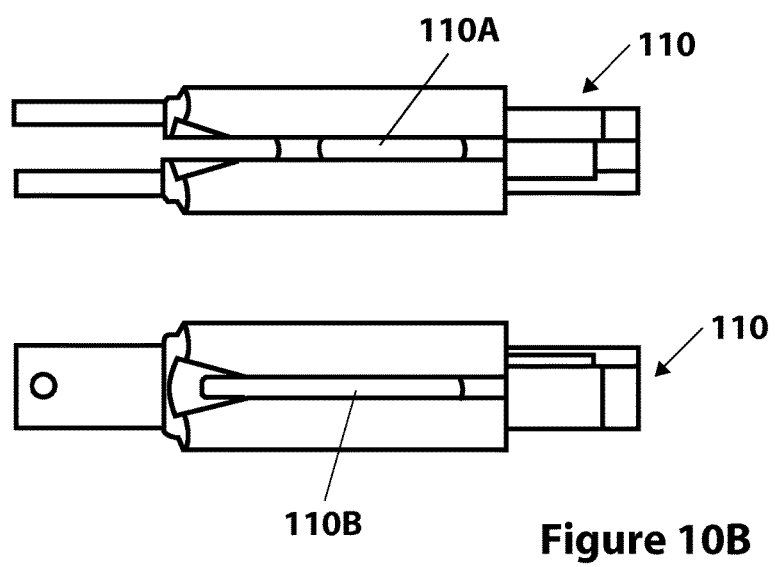
FIG. 10B depicts exemplary embodiments of the surgical device having sterilizable improvements to the end effector and access ports in the housing for comparison with the views of FIG. 10A.

FIGS. 10A-B show exemplary embodiments of the surgical device having sterilizable improvements to the end effector 110 and access ports in the housing. Reusable tools are increasibly attractive to medical facilities due to the cost sensitive point of care economics associated with them. As shown in FIG. 10A, the internal components of previous end effectors 110 may be difficult to access and clear of bioburden during the cleaning and resterilization process. As depicted in FIG. 10B, the present improvements to the end effector 110 housing allow for more access and greater ease of clearing bioburden. As is apparent in FIG. 10B, in these embodiments the surgical device has additional ports 110A, 110B in the end effector integral housing 110 to allow a cleaning agent to pass through to the inner components.

Figure 11A:
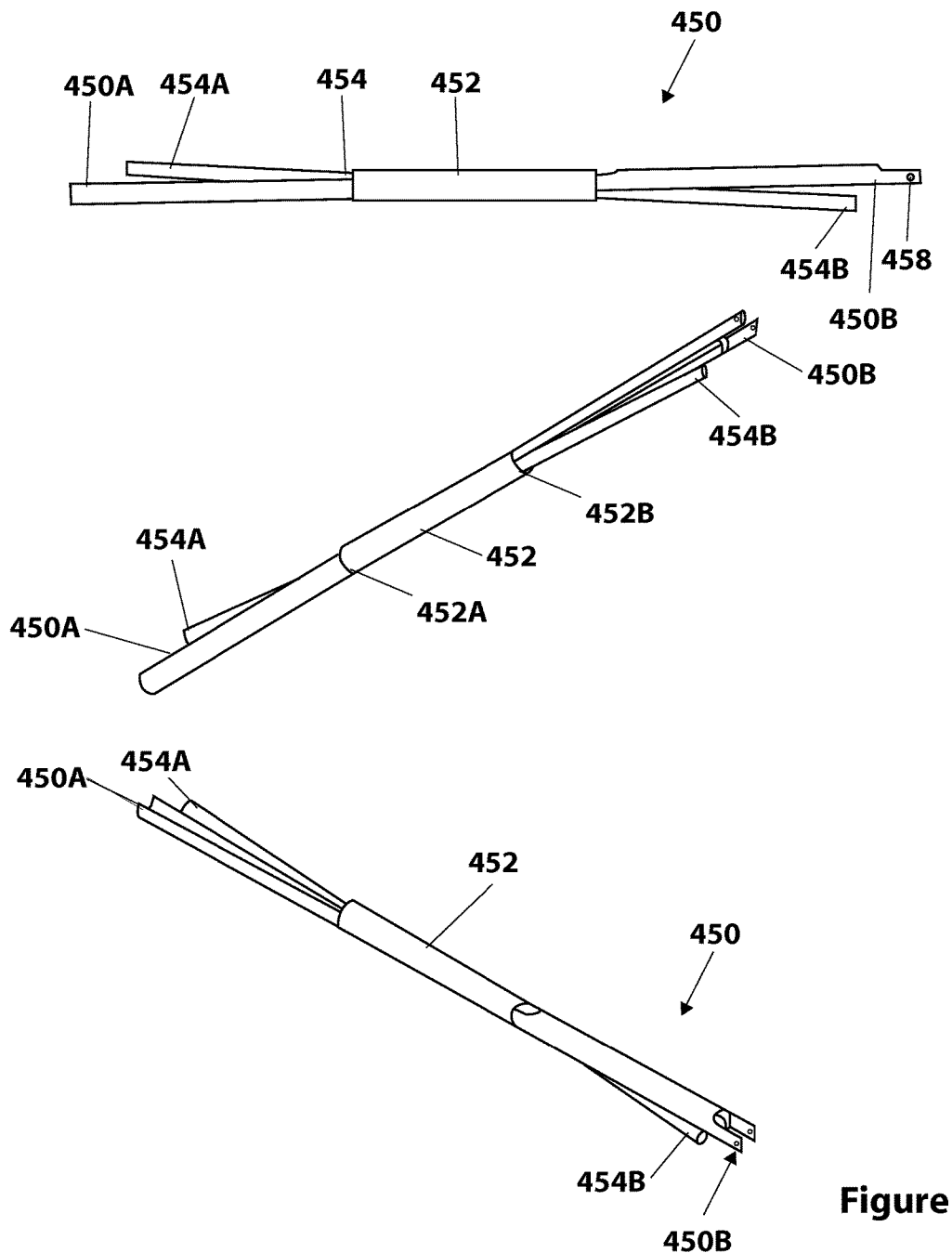
FIG. 11A depicts various views of certain implementations of the surgical device comprising further improvements in the introduction process embodied in improved introducers, according to one embodiment.
Figure 11B:
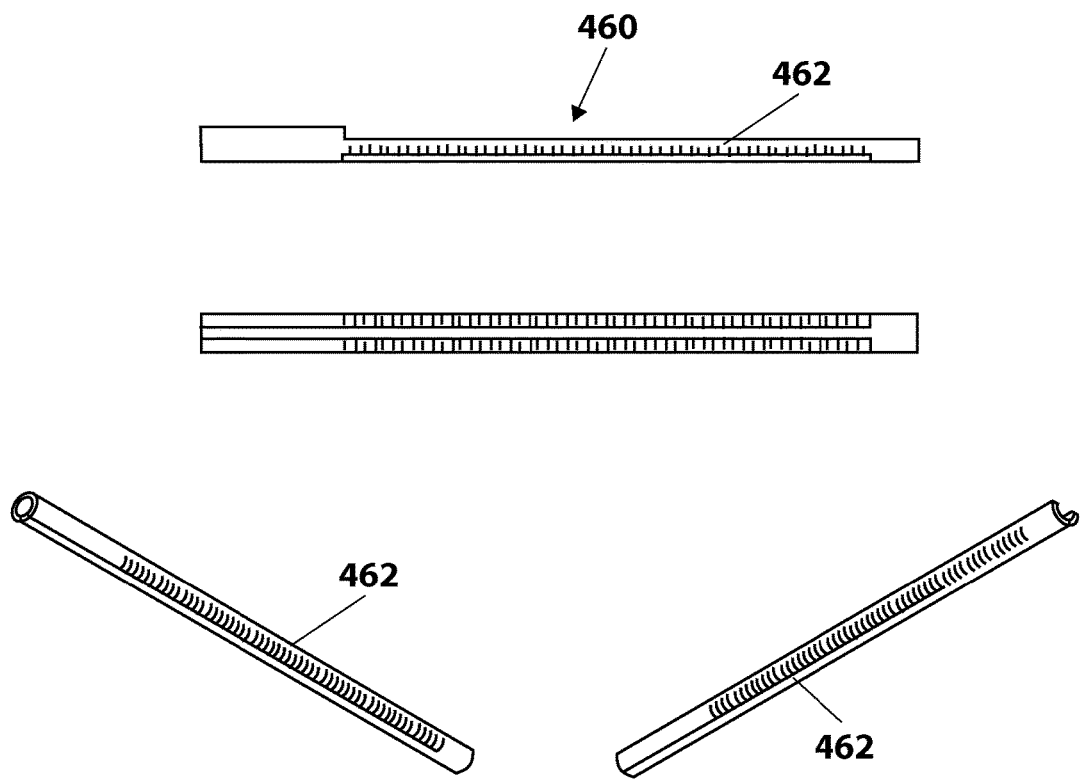
FIG. 11B depicts various views of certain implementations of the surgical device comprising further improvements in the introduction process embodied in improved introducers, according to one embodiment.

Certain implementations of the surgical device comprise further improvements in the introduction process embodied in improved introducers, as depicted in FIGS. 11A-11B. FIG. 11A depicts one embodiment including an introduction device 450 and a laparoscopic device 454 having a camera (also referred to herein as a "scope" or "camera scope"), both of which are positioned through a trocar (also referred to as a "port") 452. That is, as described in detail below, the introduction device 450 and camera scope 454 are configured such that both can fit through the trocar 452 and are sufficiently moveable in relation to each other while positioned through the trocar 452 to allow for performance of the desired surgical procedures as described herein.

Typically, fitting both a camera and a surgical device through a trocar forces surgeons to use a larger or multiple ports/trocars, which may inhibit motion and may cause collisions between the introduction and camera devices within the surgical cavity.

In contrast, the over camera introducer 450 implementation variously shown in FIG. 11A utilizes a single port/trocar 452 in the umbilicus for the camera scope 454 as well as the introduction device 450, thereby reducing the total number of ports required and reducing the complications inherent therein. To alleviate the various issues encountered by larger or multiple ports, the embodiments depicted in FIGS. 11A and 11B comprise an over-the-camera introducer 450 configured to allow a camera or laparoscopic device (such as camera scope 454) to pass through a trocar 452 of minimal size along with one or more toolheads while maintaining the ability to move both devices independently. In these embodiments, the introducer 450 is inserted into the trocar 452 and, as best shown in FIGS. 11A, 20, 22A-22C, and 23A-23C, comprises complementary slots, or receiving channels 450A, 450B which are defined within the introducer 450 and extend substantially past the opposing ends of the trocar 452. In these embodiments, the receiving slots 450A, 450B are configured so as to allow passage of the scope 454 through the center axis of the trocar 452 and to cradle the scope 454 when it is at the offset, rather than coaxial, position, as shown in detail in FIGS. 17A-21B. That is, the receiving slots 450A, 450B are configured to receive portions of the scope 454 when both the introducer 450 and scope 454 are positioned through the trocar 452. In such embodiments, these slots 450A, 450B are thus aligned to allow for the cylindrical camera scope tube 454A, 454B to be concentric or coaxial with the introduction device shaft 450, 450A, 450B and extend outwardly from the proximal 454A and distal 454B ends. In these applications, the scope tube 454 can deflect in plane with the introduction shaft 450, such that the scope 454 is coaxial with the introduction shaft 450 during introduction, and then be deflected during operation by the user during use.

Figure 19:
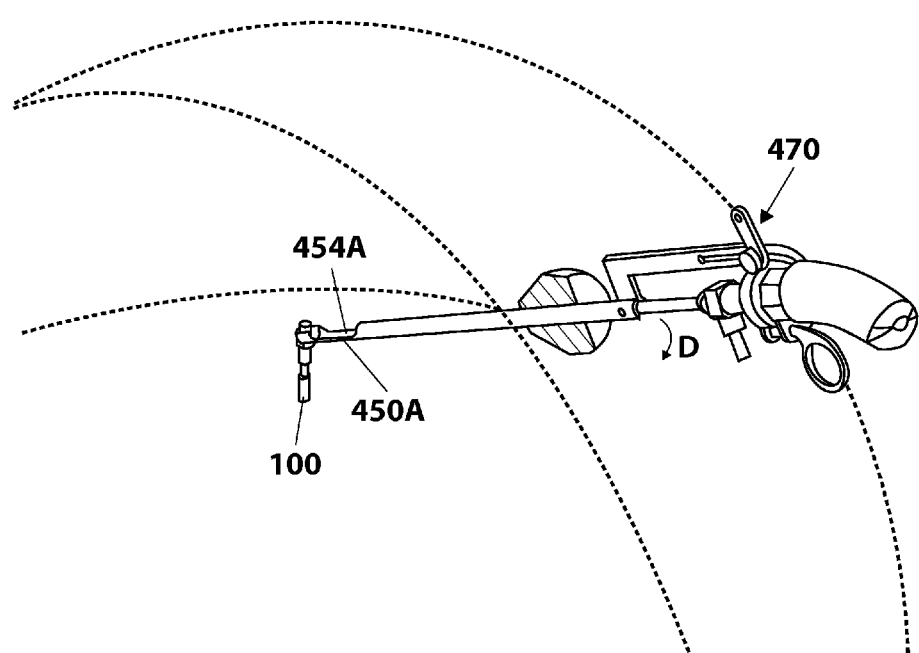
FIG. 19 depicts a perspective cutaway view of the camera and introduction device having been returned to their original orientation, according to one embodiment of the system.
Figure 20:
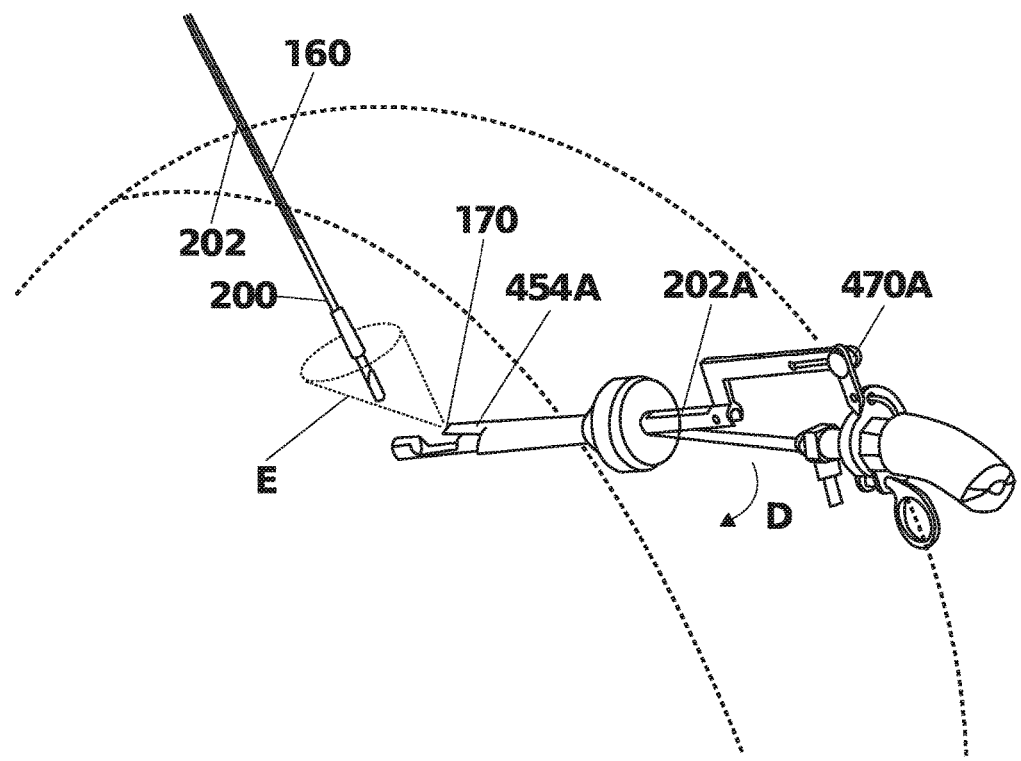
FIG. 20 depicts a perspective cutaway view of an embodiment of the system with the scope displaced and the beveled end of the scope oriented in the direction of the desired entry site of a handle tool.
Figure 21A:
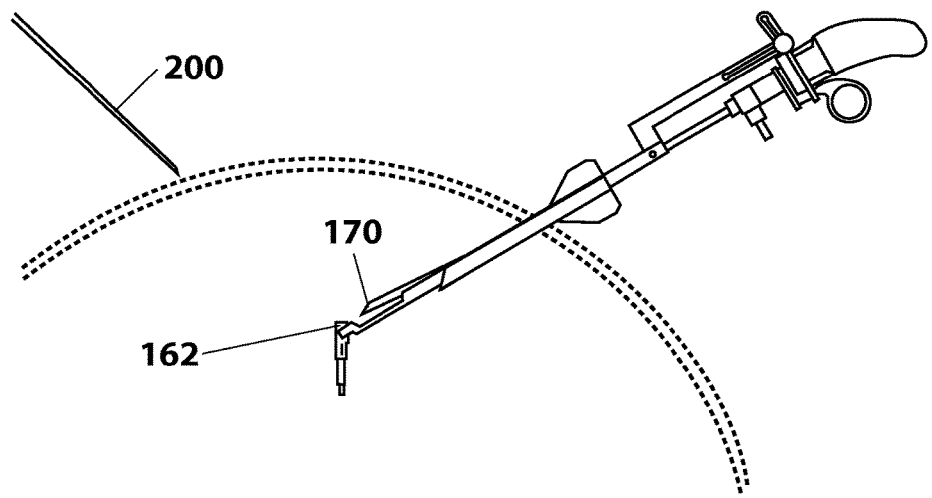
FIG. 21A shows a side view of the insertion of a cannula shaft for mating with an end effector, according to an exemplary embodiment.
Figure 21B:
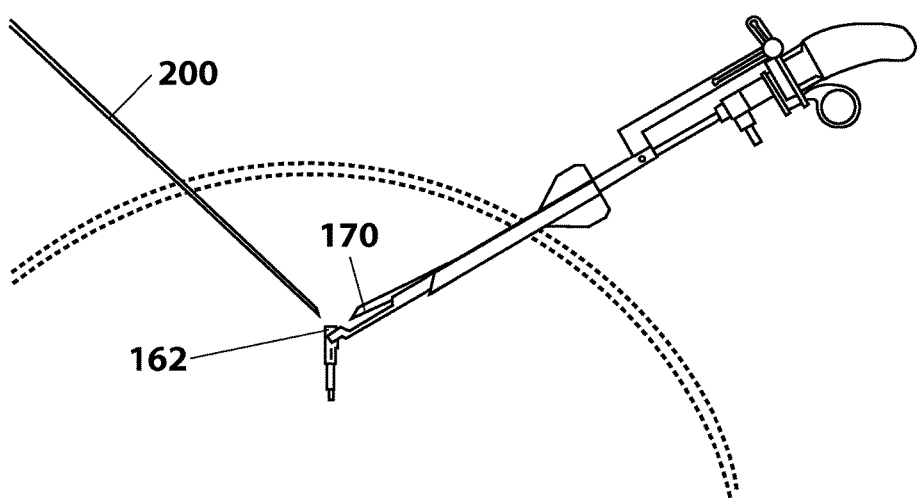
FIG. 21B shows a further side view of the insertion of a cannula shaft for mating with an end effector, according to an exemplary embodiment.
Figure 22A:
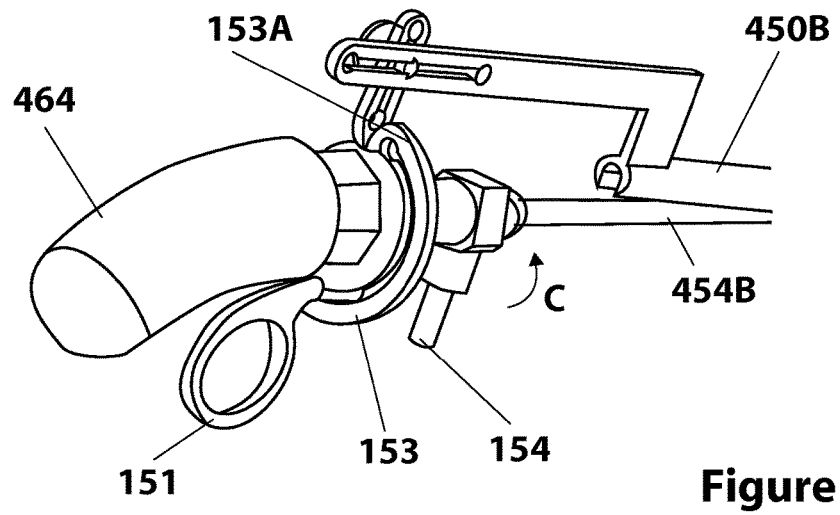
FIG. 22A depicts a perspective view of the camera and proximal operation handle operating with the introduction device, according to one embodiment.
Figure 22B:
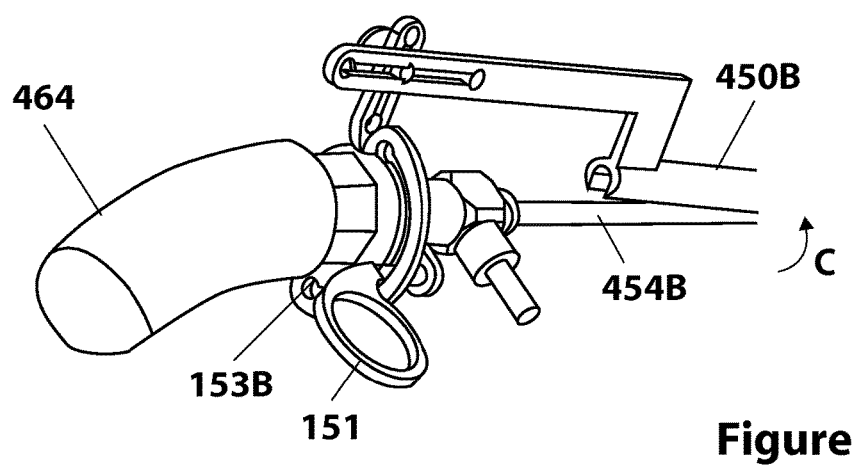
FIG. 22B depicts a perspective view of the camera and proximal operation handle in mid-rotation, according to one embodiment.
Figure 22C:
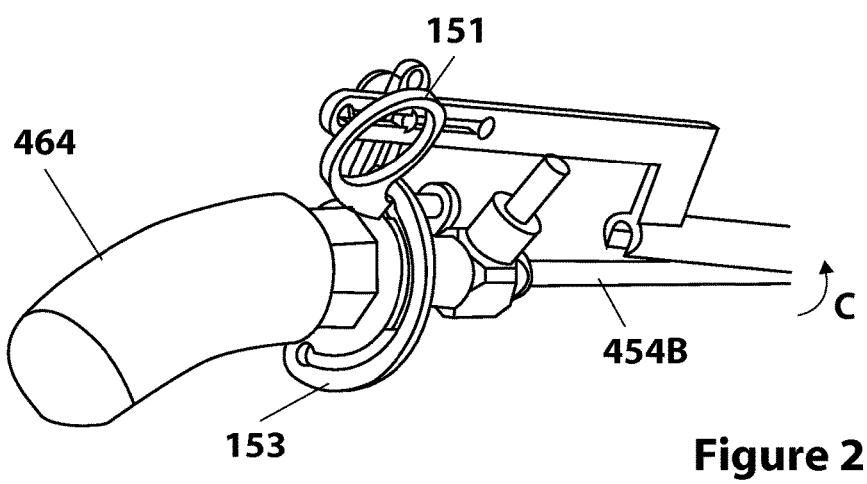
FIG. 22C depicts a perspective view of the camera and proximal operation handle following rotation relative to the camera, according to one embodiment.

In use, as further described in FIGS. 19-20, scope movement is constrained by the overlapping channels 450A, 450B and the diameter of the trocar 452. In certain embodiments, the openings 452A, 452B on opposite sides of the shaft 452 allow the camera scope 454 to be rotated about a moving point in the central shaft of the introducer 450 at the location wherein the slots 450A, 450B are connected. In various embodiments, the length of the overlap between the two slots 450A, 450B determines how the range of motion wherein the introduction device 450 can translate in and out of the trocar 452 when the camera shaft 454 and introduction device 450 are not concentrically aligned. The camera 454 and the introduction device 450 can be moved completely independently of each other, with the camera 454 movement primarily limited by contact with the trocar 452 and introduction device channels 450A, 450B.

Certain further embodiments of the surgical device comprise additional improvements to further address constrained introducer and camera orientations. Certain prior art embodiments require that the rotational, axial and separation orientations for the introduction device, laparoscopic device, and camera all be controlled and maintained simultaneously by the user Implementing a system that can selectively alleviate such constraints can reduce the operator burden and simplify surgical procedures. The system of FIG. 11A maintains the vertical plane of the camera view with that of the introducer shaft 450. Thereby the primary axis of both camera and scope is maintained such that the scope can be displaced from the introducer shaft in a controlled fashion. In various embodiments, the scope may also be controllably rotated relative to the camera view to change the orientation of the scope bevel, changing the angle of the camera view. Thus, in these implementations, the entire system is designed so that it can be placed through a single trocar.

According to another embodiment, depicted from various perspectives in FIG. 11B, the surgical device comprises a deformable introduction device 460 similar to the over-the-camera embodiment described in reference to FIG. 11A. In these embodiments, the deformable introduction device 460 is configured to accommodate a camera and scope and reduce the size of the port required to accommodate both devices. It is understood that in these embodiments, the deformable introduction device can be substituted for other introduction devices described herein. In these embodiments of the introduction device may further comprise an interface which supports the end effector assembly at one end, and a handle assembly to allow the manipulation of the device from the exterior of the patient, as described variously elsewhere herein. In these embodiments, the tube of the introduction device has a region 462 designed to be selectively deformed away from the central axis of the introducer by the application of user force. In exemplary embodiments, deformation is only possible in a designated direction as a means of reducing errors. When the introduction device 460 is inserted and the end effector is presented into the body, the compliant portion of the introduction device tube is deformed to move the end effector assembly away from the camera and the centerline of the introduction device. This offset between the camera and the end effector creates the triangulation necessary for a surgeon to perceive depth and to reposition the end effector easily.

FIGS. 12A-15B show various exemplary embodiments of the handleset 300 that provide the operator with the ability to place and hold the locking features of the inner and outer cannula shafts in the "alignment position" or "closed position" as shown in FIG. 16A-16D. In these embodiments, and by way of reference, the surgical device further comprises a distal handle 302, a distal handle cover 304, a proximal handle 306, a proximal handle adjuster 308, a locking slide 310, a rotation knob 312, a detent spring 314, and a toggle switch 316.

Certain exemplary embodiments of the surgical device have an "alignment position" or "closed position," described further herein and depicted in FIGS. 16A-16D. In exemplary embodiments in this position, (or "state"), the distal channel features of the inner (or "active") cannula shaft 1000 and the outer cannular shaft 1002 ("cannula shaft") correspond to the position of the engaging features of the end effector 100. In these states, the control shaft can be engaged properly to the end effector 100. If the distal channel features of the inner and outer shafts are not in the proper alignment engagement between the control shaft and the end effector can be difficult or possibly damaging to the interfacing components. Therefore it is important that the "alignment position" be easily and reliably achieved and maintained.

Figures 12A, 12B:
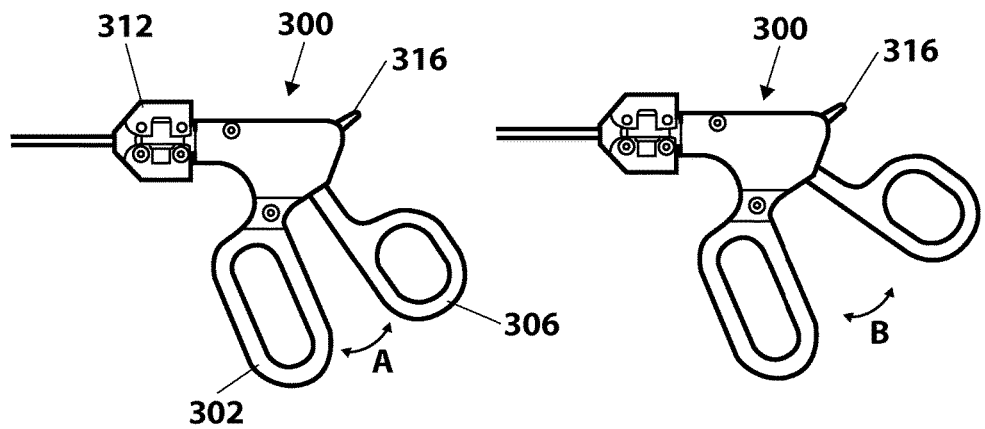
FIG. 12A depicts a side view of an exemplary embodiment of the handleset according to one implementation.
FIG. 12B depicts a side view of an exemplary embodiment of the handleset according to one implementation.
Figures 12C, 12D:
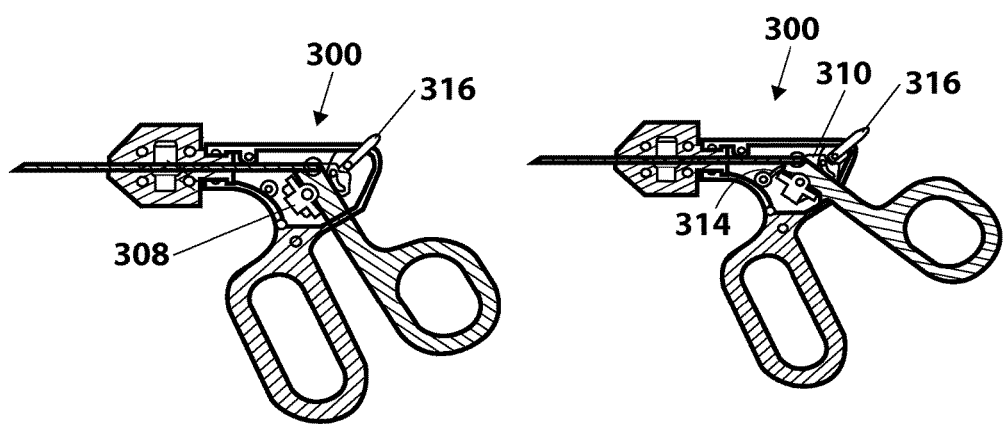
FIG. 12C depicts a cross sectional view of the handleset of FIG. 12A, according to one embodiment.
FIG. 12D depicts a cross-sectional view of the handleset of FIG. 12B, according to one embodiment.
Figure 13:
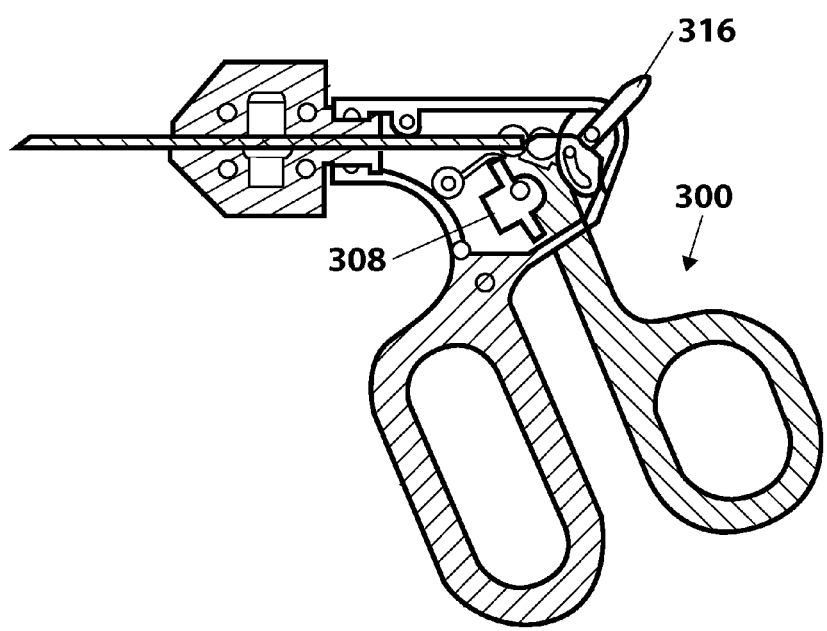
FIG. 13 depicts a cross-sectional view of the handleset in an "overthrow" position, according to an exemplary embodiment.

FIGS. 12A and 12B show a sideview of the handle assembly various configurations. FIG. 12A depicts the handle in the in the "closed" position (designated with reference letter A, and shown in the end effector in FIG. 16A). In this position, the distal end of the active shaft 1000 is aligned with the distal end of the outer shaft 1002. FIG. 12B depicts the "open" position (designated with B, shown in FIG. 16B, wherein the active shaft 1000 slides distally relative to, and extends beyond the outer shaft 1002). FIGS. 12C and 12D show a crosssectional view of the handleset assembly in the same states.

Figure 16A:
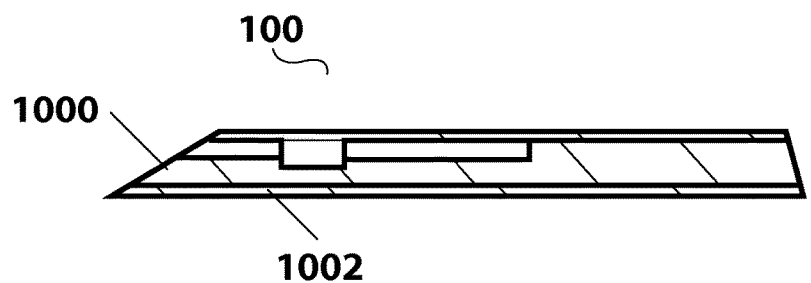
FIG. 16A depicts a cross-sectional end of the cannula tip according to one embodiment, wherein the tip is in the closed position.
Figure 16B:
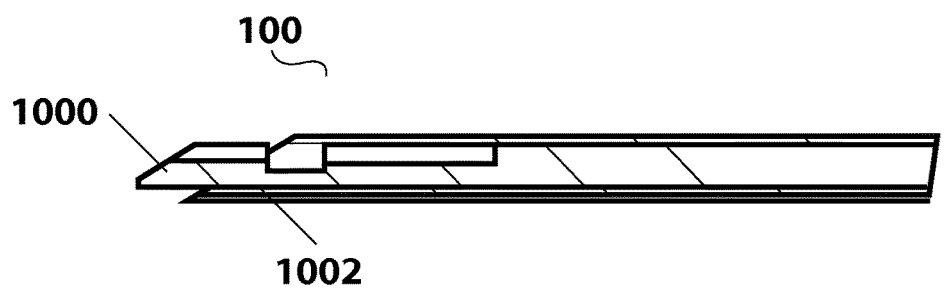
FIG. 16B depicts a cross-sectional end of the cannula tip according to one embodiment, wherein the tip is in the open position.
Figure 16C:
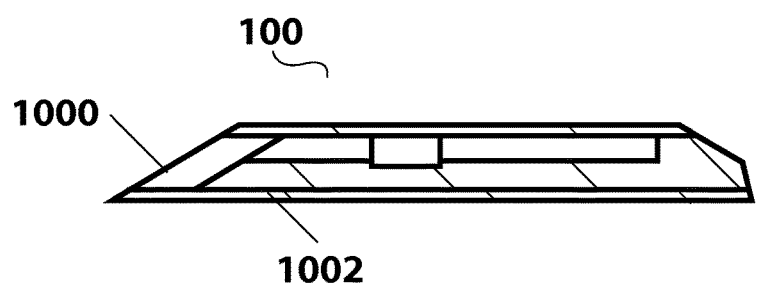
FIG. 16C depicts a cross-sectional end of the cannula tip according to one embodiment, wherein the tip is in the overthrow position.

With the toggle switch 316 in the "up" position the proximal handle 306 is free to move from the "open" position to through the "alignment position" to the "overthrow position" (best shown in FIGS. 13 and 14C) where the end of the inner shaft is displaced further inward relative to that of the outer shaft, as shown in FIG. 16C. The "overthrow position" allows for additional grip force in the handleset 300.

Figure 16D:
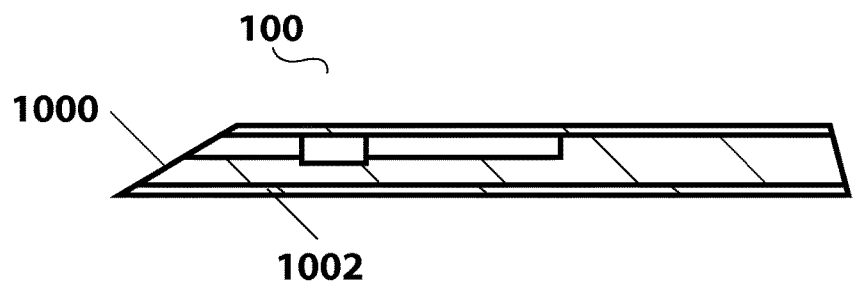
FIG. 16D depicts a cross-sectional end of the cannula tip according to one embodiment, wherein the tip has returned to the closed the position.

In the "alignment position", the groove features of the distal tip of the inner shaft 1000 are once again aligned with that of cannula shaft 1002 (as shown in FIG. 16D) and the toggle switch 316 (or part within the mechanism, such as the slide lock) can be engaged by a spring detent, providing tactile resistance to being repositioned and maintaining the position set by the user, as described in relation to FIG. 16A-16D. In certain embodiments, the handle need not be placed into the alignment position for the toggle switch to be operated.

Figure 14A:
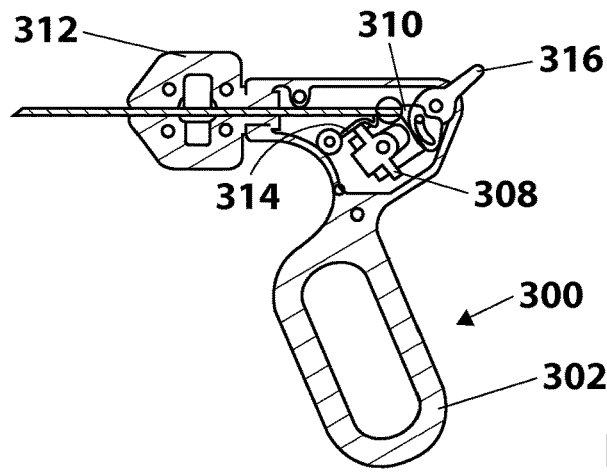
FIG. 14A depicts a cross-sectional view of an exemplary embodiment of the handleset in the "closed" position.
Figure 14B:
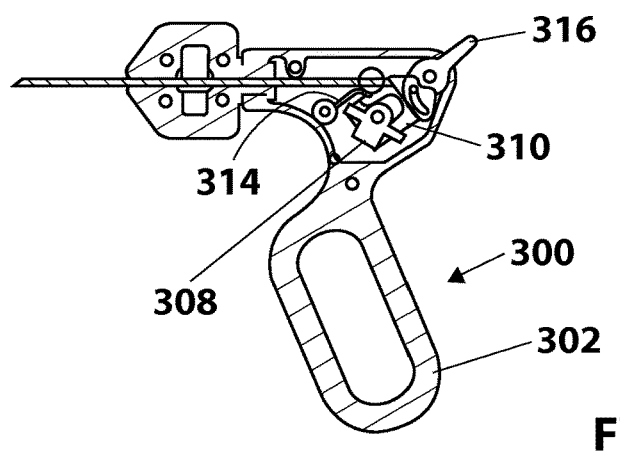
FIG. 14B depicts a cross-sectional view of an exemplary embodiment of the handleset in the "open" position.
Figure 14C:
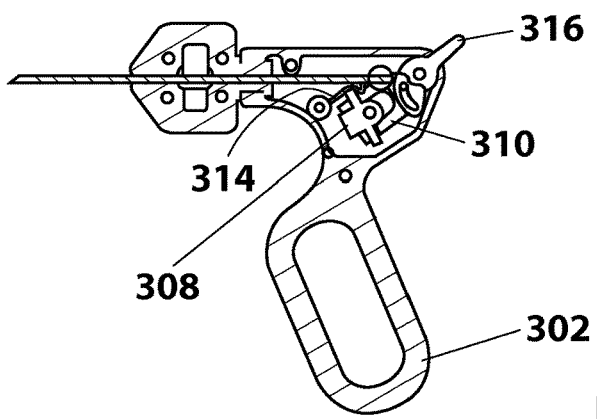
FIG. 14C depicts a cross-sectional view of an exemplary embodiment of the handleset in the "overthrow" position.

The proximal handle 306 can be adjustably attached to an alignment component 308, as shown in FIGS. 14A-14C (wherein the proximal handle is removed). FIGS. 14A-14C show the alignment component in the "closed" (FIG. 14A), "open" (FIG. 14B) and "overthrow" (FIG. 14C) positions respectively.

Figure 15A:
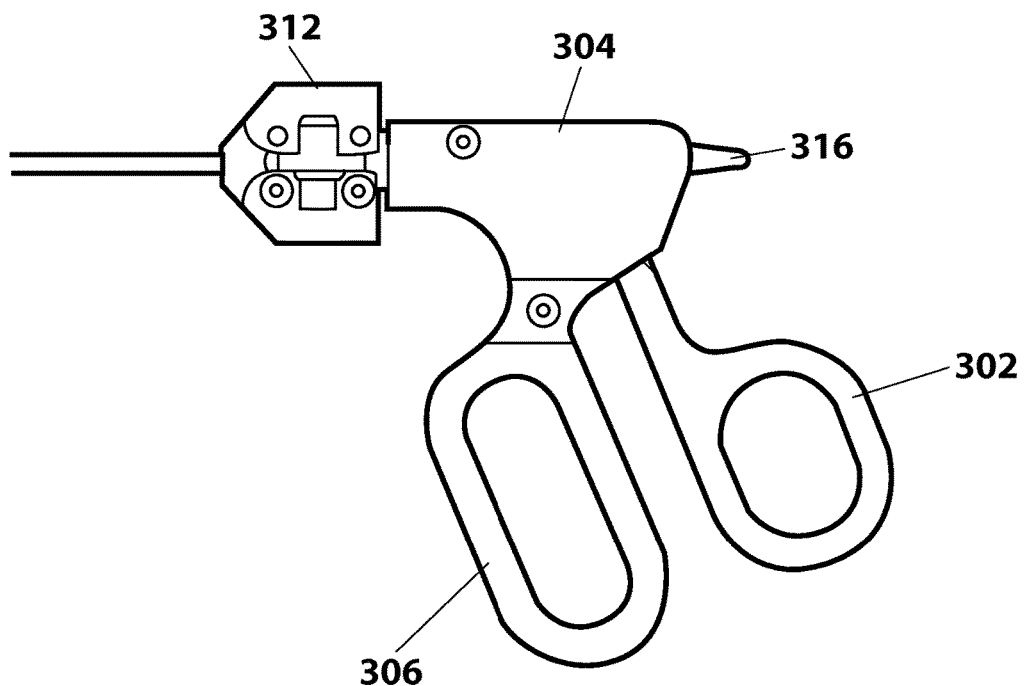
FIG. 15A depicts a side-view of an exemplary embodiment of the handleset according to one implementation wherein the toggle switch is in a down position.
Figure 15B:
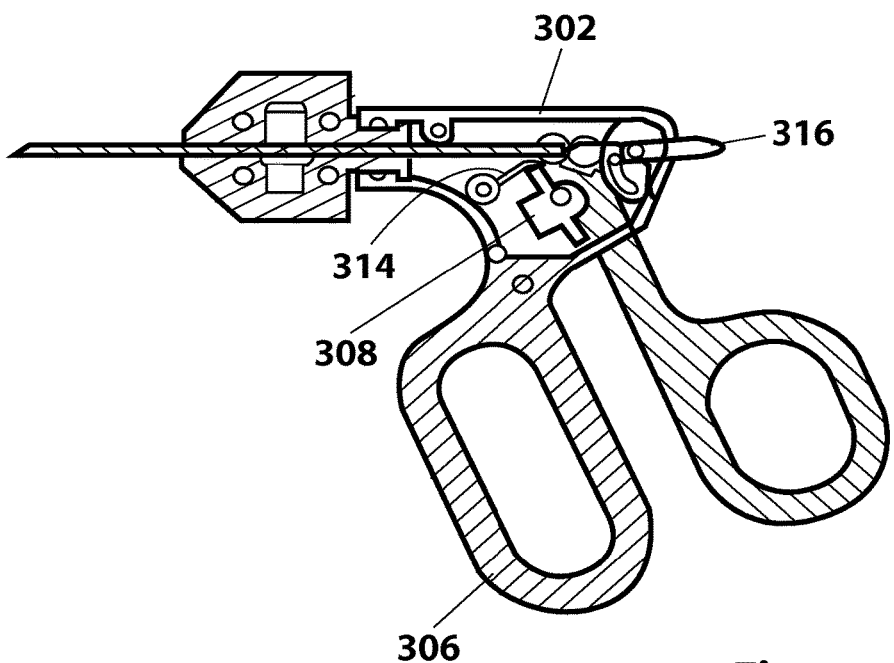
FIG. 15B depicts a cross sectional view of an exemplary embodiment of the handleset according to one implementation wherein the toggle switch is in a down position.

When the user switches the toggle switch from the "up" position to the "down" position it actuates the alignment slide 310 and forces the proximal handle 306 to move to the state that puts the inner and outer shaft in the "overthrow position" (as best shown in FIG. 15B). In operation, while the toggle switch 316 is in the "down" position, and the proximal handle is constrained in the "alignment position."

The toggle switch 316 or internal alignment features of the handle set can also engage an elastic detent feature 314 to provide additional haptic feedback to the user and help maintain one of the two toggle states.

Figure 17A:
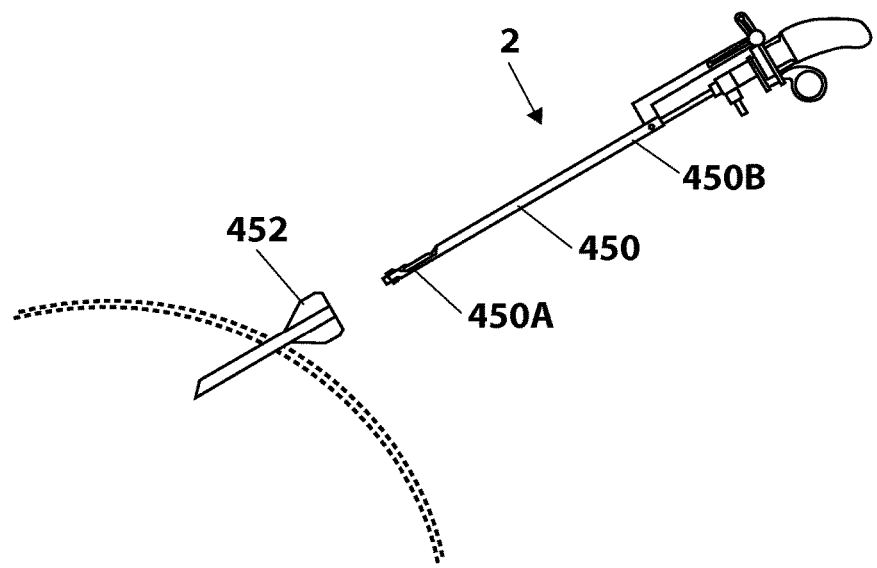
FIG. 17A depicts a side view of the perpetration for insertion of the introduction device into a trocar, according to one embodiment.
Figure 17B:
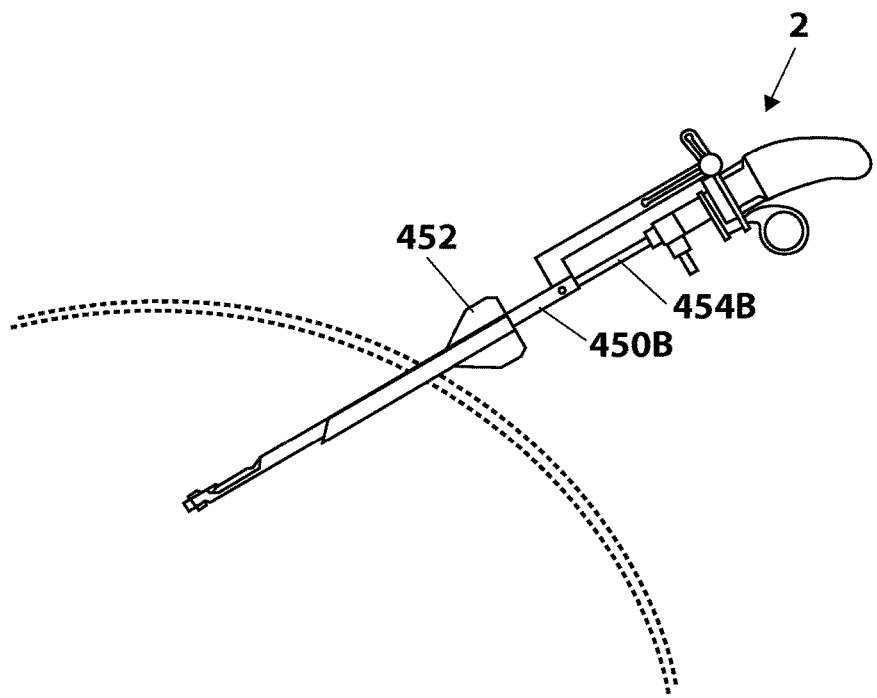
FIG. 17B depicts a side view of the insertion of the introduction device into a trocar, according to the embodiment of FIG. 17B.

FIGS. 17A-17B depict the placement of a scope surgical device 2 according to an exemplary embodiment. In these embodiments, the scope shaft 454A, 454B is introduced by way of a novel introducer shaft 450, as described in relation to FIGS. 11A-11B. As discussed herein in relation to FIG. 11A, it is a principle object of the system to provide an introduction system which allows the user to align the scope/camera and surgical tools inside the cavity of a patient. Critically, in exemplary embodiments of the system, the scope is introduced in such a way as to be easily positionable at the distal scope end by way of the proximal handle to increase the ease of placement and otherwise facilitate the ease of the procedure. In certain embodiments, the distal scope end further comprises a bezel, though that is in no way necessary for the function of the device.

Figure 18A:
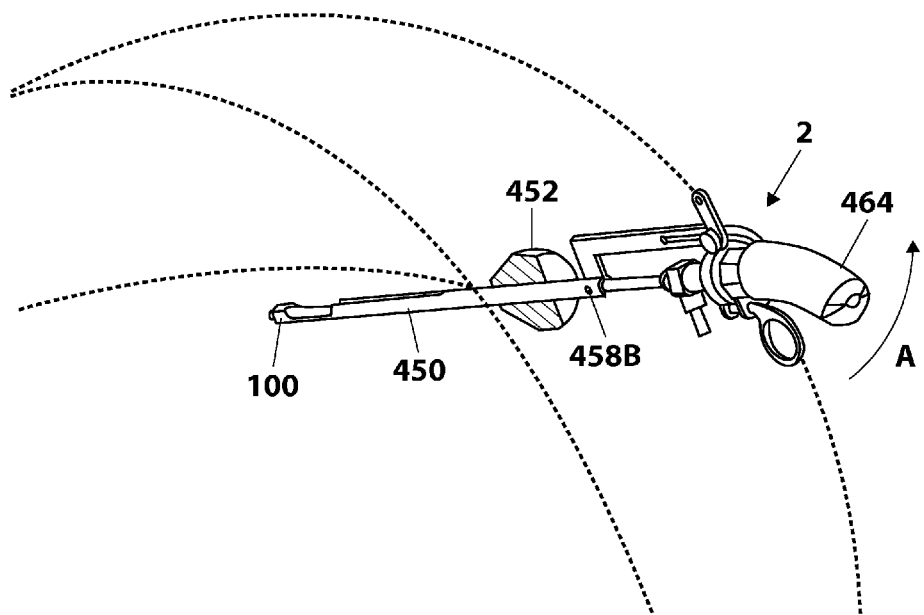
FIG. 18A shows a perspective cutaway view of the insertion of FIG. 17B.
Figure 18B:
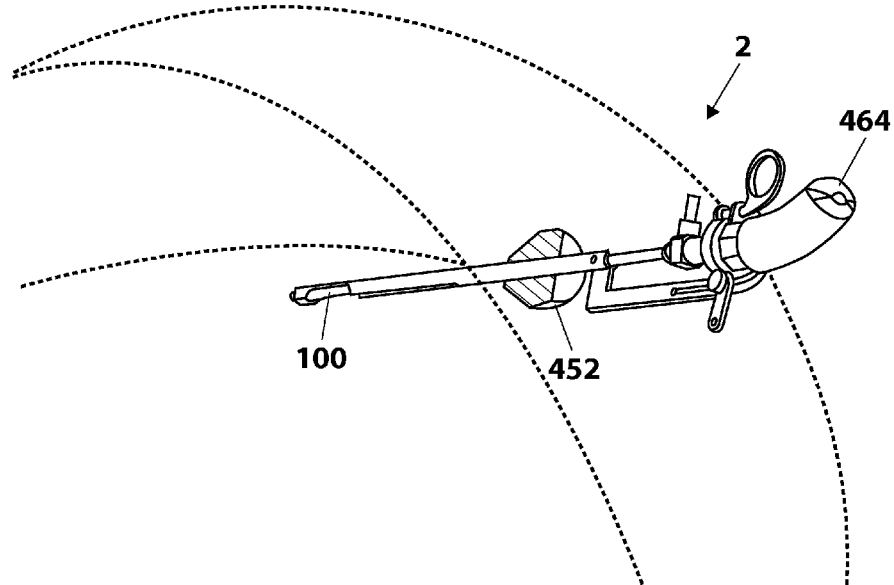
FIG. 18B shows a perspective cutaway view of the rotation of the camera and introduction device relative to the trocar, according to the embodiment of FIG. 17A.
Figure 18C:
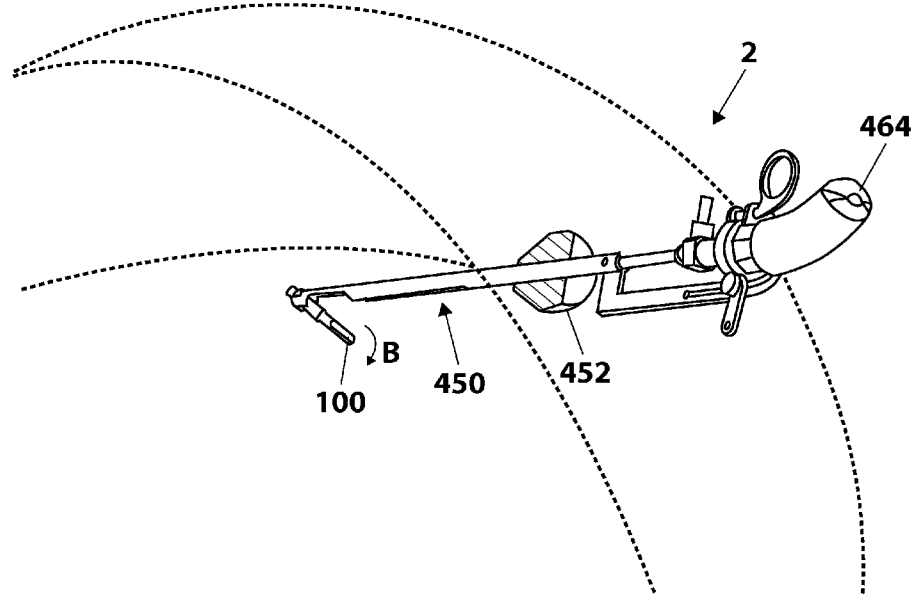
FIG. 18C depicts a perspective cutaway view of the embodiment of FIG. 18B, wherein the end effector is moving relative to the force of gravity.

In exemplary embodiments of the surgical system, the axis of the scope 454 and the camera 464 are independently rotatable around the axis so as to orient the bezel freely about the horizon of the camera for directed viewing. In certain embodiments, the rotation of the scope and camera can be fixed so as to maintain that orientation during rotation of the camera. As shown in FIGS. 18A-18C, rotating the entire assembly (by rotating the camera 464—designated by reference letter A) orients the introducer shaft 450 such that the end effector 100 is free to rotate around the axis of the tool holder due to gravity or other external force (designated by reference arrow B). Rotating the assembly back to the original orientation completes the deployment of the end effector, as is shown in FIG. 19. As is shown in FIG. 18C, upon completed deployment, the end effector 100 may be capable of axis movement relative to the introducer shaft 450. This is described further in reference to FIG. 19.

As shown in FIG. 19-20, releasing the connection 470 between the introducer shaft 450 and the camera 464 allows the end of the scope 454A to be axially deflected or displaced (shown by reference letter D), relative to the introducer shaft 450A. Re-fixing the connection in the new position 470A then maintains the displaced orientation. As shown in FIG. 20, with the scope displaced and the beveled end 170 of the scope oriented in the direction of the desired entry site 160, the insertion of the cannula shaft 200 can be monitored by the user in the theater of operation, as is depicted by the cone labeled E.

FIG. 20 also depicts an implementation further comprising an alignment indicator 202 on the cannula shaft 200 as well as a visual indicator 202A on the introduction shaft 450. The process of engaging the toolhead with a cannula shaft and removing it from the introducer is eased when the central axis of the cannula is in the rotational plane of the tool holder. In exemplary embodiments, this can be achieved if the introducer shaft 450 is rotated so that the tool holder rotation plane is pointing towards the insertion point 160 of the cannula shaft. A visual indicator 202A on the proximal portion of the introducer shaft 450 is thus used to provide this indication.

Once the cannula 200 has been inserted the bevel 170 of the scope can be reoriented to face the end cap of the end effector by releasing the connection between the camera and the scope and re-securing it in the rotated position as shown in FIGS. 21A-22D. These figures also show the scope being used to "spot" the insertion of the cannula shaft through the abdominal wall to ensure that nothing is obstructing the insertion.

As shown in FIGS. 22A-23F, in certain embodiments, the orientation of the scope angle can be manually rotated (designated with reference letter C), by manual rotation of the proximal operation handle 151. In certain embodiments this operation handle is in the form of a ring, as shown, however other embodiments are possible. In certain embodiments, the surgical device further comprises a rotation guide 153. In yet further embodiments, the rotation guide further comprises detent stops 153A, 153B, which allow the user tactile feedback as to the position and/or locking of the scope angle. Certain embodiments of the surgical device comprise a light source attachment 154, as is well-established in the art.

Figure 23A:
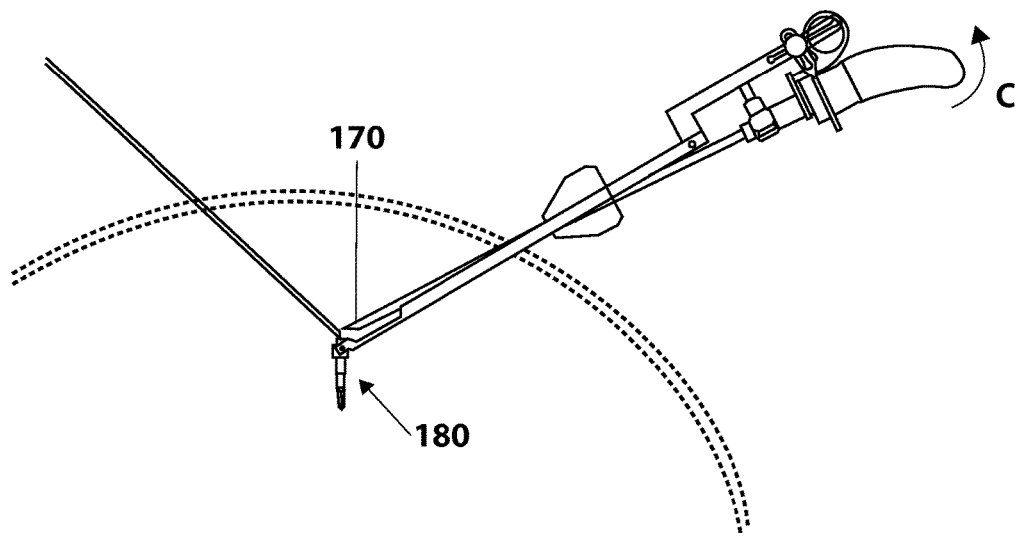
FIG. 23A shows a side view of the insertion of a cannula shaft for mating with an end effector, wherein the camera shaft is in a deflected position, according to an exemplary embodiment.
Figure 23B:
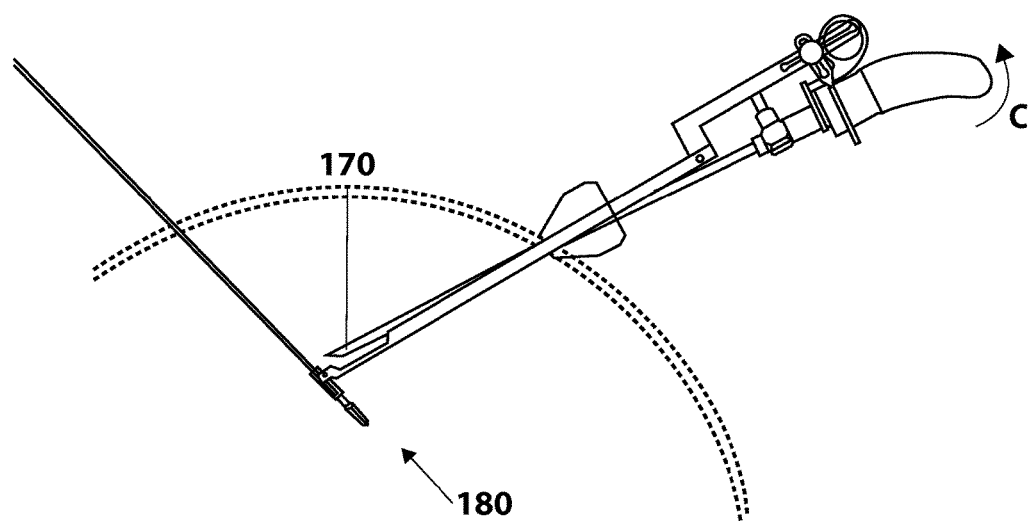
FIG. 23B shows a further side view of the insertion of a cannula shaft for mating with an end effector, according to the embodiment of FIG. 23A.
Figure 23C:
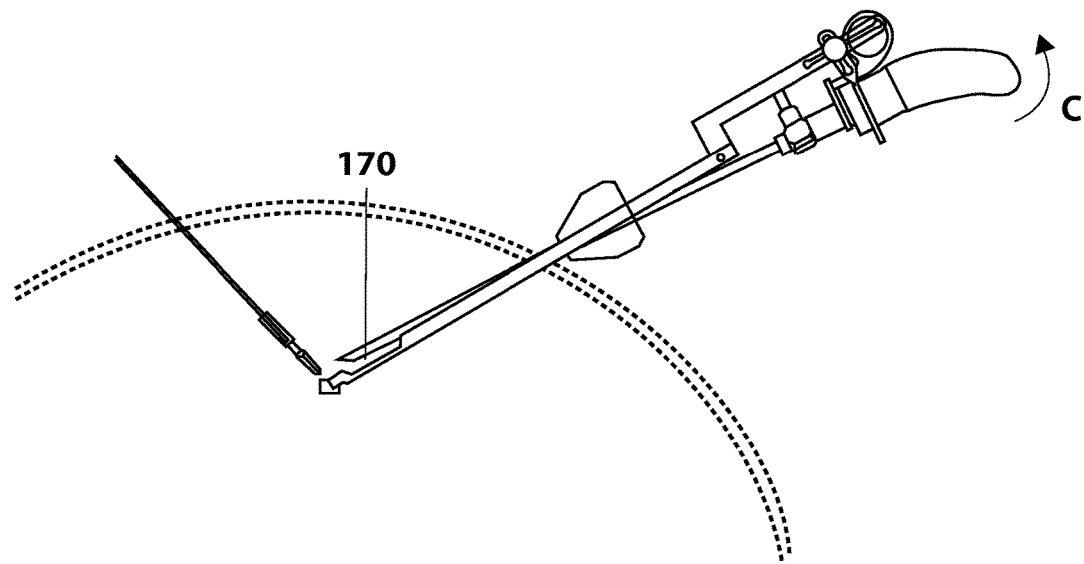
FIG. 23C shows a side view of the successful mating of the cannula shaft with an end effector, wherein the camera shaft is in a deflected position, according to the embodiment of FIG. 23A.
Figure 23D:
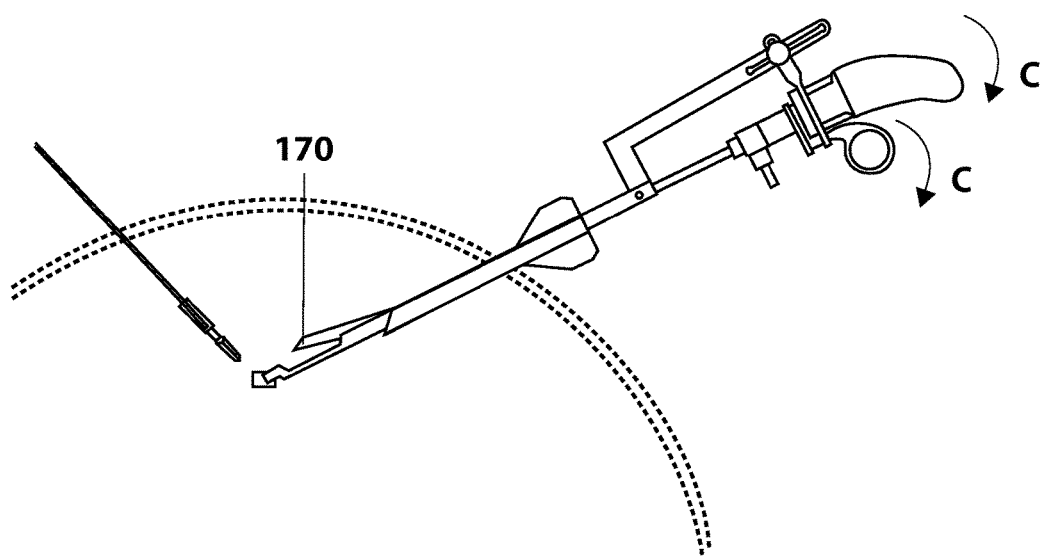
FIG. 23D shows a further side view of the embodiment of FIG. 23A, wherein the camera shaft has been rotated.

The rotation of the proximal operation handle 151 is in operational and rotational communication with the scope shaft such that the distal scope bezel 170 may be oriented toward the cannula guide cap 162, as is shown for example in FIG. 23B. With the scope bezel 170 pointing towards the cannula guide cap 162 the insertion of the cannula point into the guide cap can be monitored and proper toolhead engagement 180 can be confirmed.

Figure 23E:
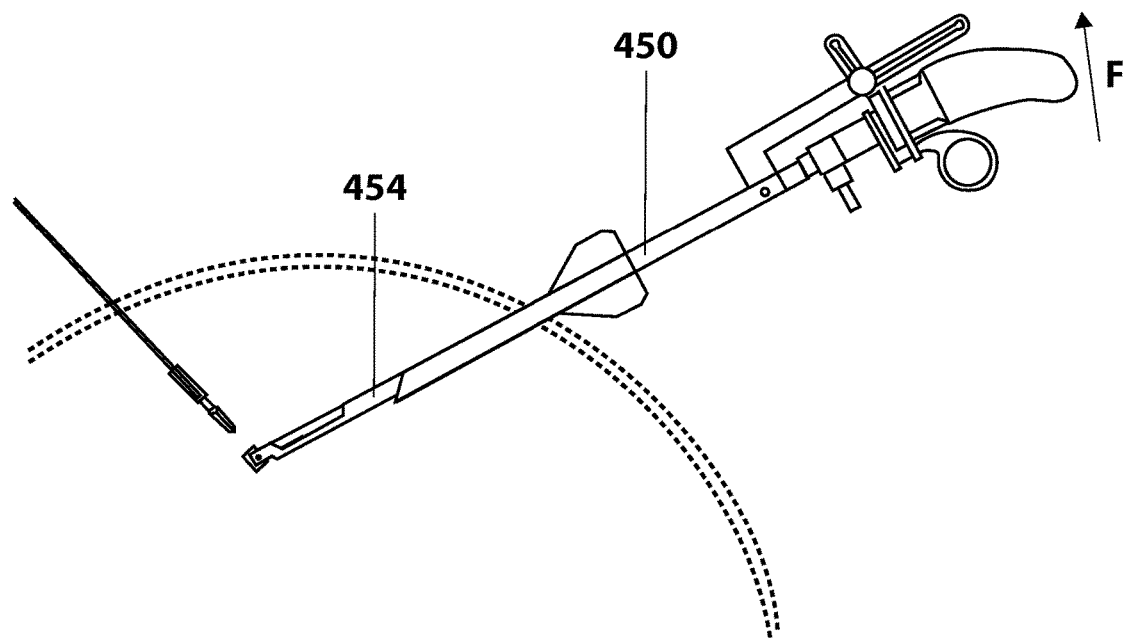
FIG. 23E shows a further side view of the embodiment of FIG. 23A, wherein the camera shaft has been returned to a coaxial position.
Figure 23F:
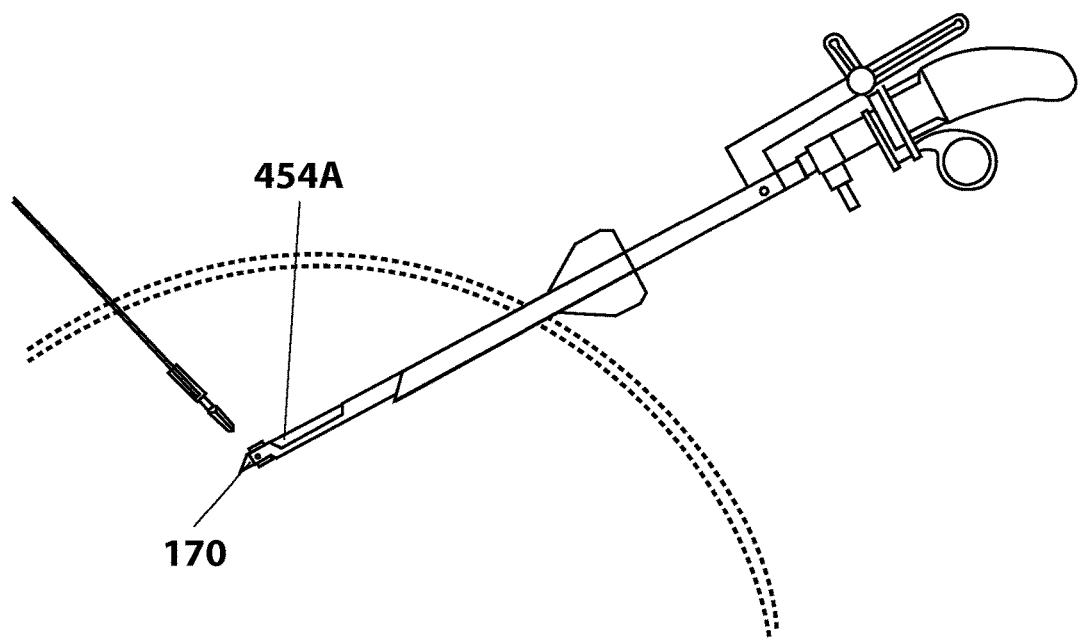
FIG. 23F shows a further side view of the embodiment of FIG. 23E, wherein the camera shaft has been extended distally through the end effector region.

Once the toolhead has been successfully removed, the connection between the introduction handle and camera holder can be loosened and the scope 454 can be repositioned so that is once again coaxial with the introducer shaft 450, the motion of which is shown as reference arrow F in FIG. 23E. The introducer shaft 450 can then be retracted or otherwise positioned along the scope. The distal end of the scope 454A is configured such that it may be accommodated through the tool holder such that the camera view 170 may be unobstructed, as is shown in FIG. 23F. Re-securing the connection between the introduction shaft and the camera holder allows the procedure to proceed in the "standard" fashion.

FIGS. 24A-32B depict various embodiments relating to improvements to the end effector 100. In certain exemplary embodiments, the surgical device comprises a single use, reloadable clip applier 120A. In certain embodiments, the clip applier 120A may feature advanced energy designs, such as monopolar and bipolar cautery implementations, a bipolar jaw comprising an outer rim for sealing and an inner rim for cutting. Certain of these embodiments further feature the use of a single use, reloadable clip.

Figure 24A:
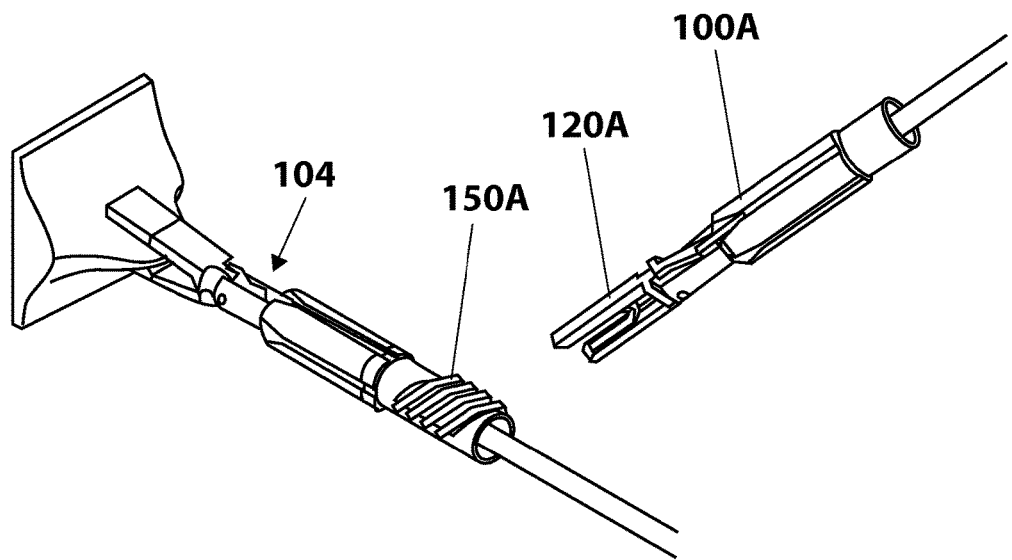
FIG. 24A depicts a perspective view of a grasper capable of holding a plurality of clips on its proximal portion for retrieval by a second surgical device having a clip applier, according to an exemplary embodiment of the surgical system.
Figure 24B:
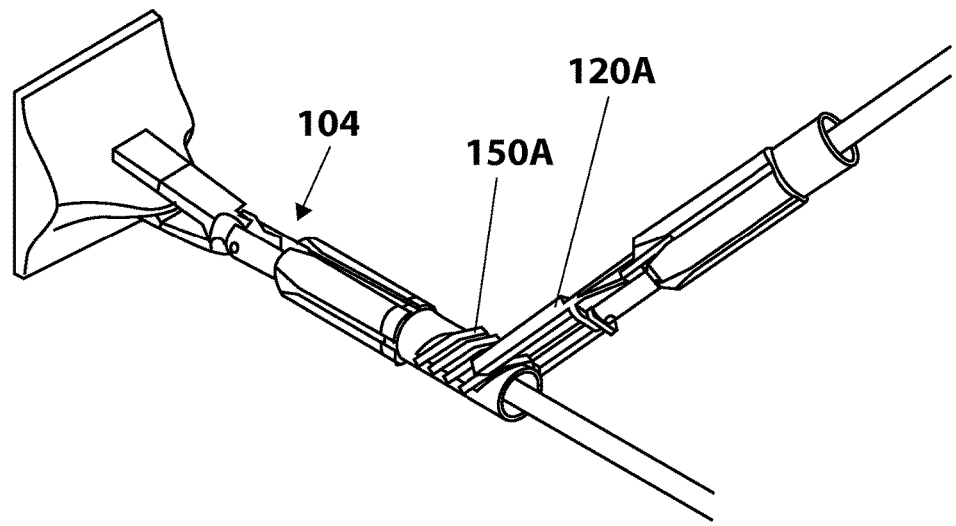
FIG. 24B depict a perspective view of the clip applier initiating coupling with a clip from the clip storage portion of the first end effector, according to the embodiment of FIG. 24A.
Figure 24C:
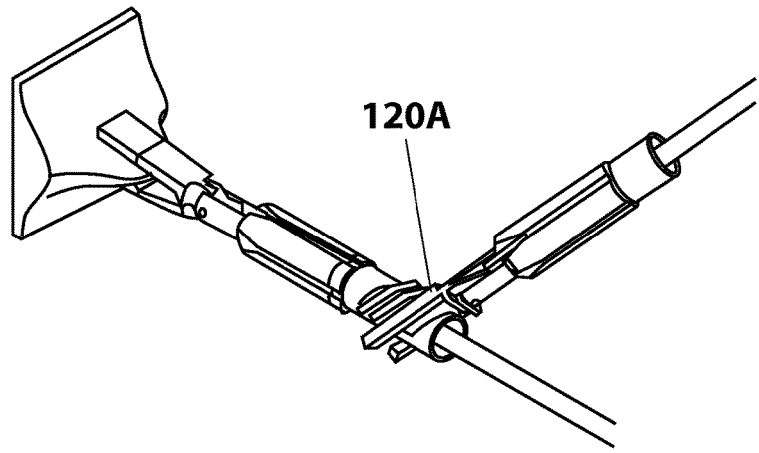
FIG. 24C depicts a perspective view of the clip applier fully coupling with a clip from the clip storage portion of the first end effector, according to the embodiment of FIG. 24A.
Figure 24D:
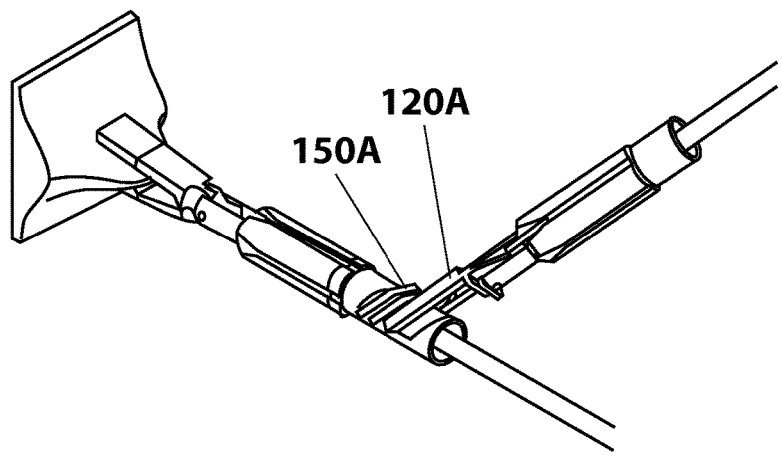
FIG. 24D depicts a perspective view of the clip applier withdrawing with a clip from the clip storage portion of the first end effector, according to the embodiment of FIG. 24A.
Figure 24E:
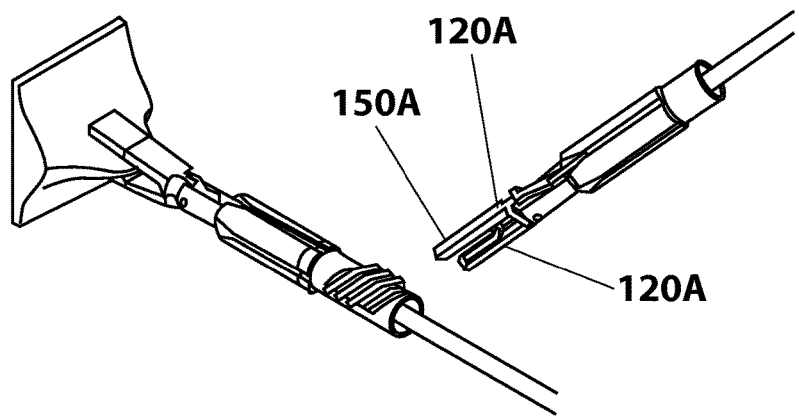
FIG. 24E depicts a perspective view of the clip applier fully withdrawn with a clip from the clip storage portion of the first end effector, according to the embodiment of FIG. 24A.
Figure 25A:
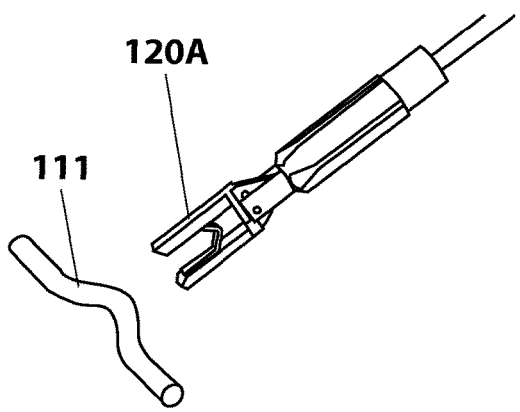
FIG. 25A depicts a perspective view of the clip applier approaching a target location, according to an exemplary embodiment of the surgical system.
Figure 25B:
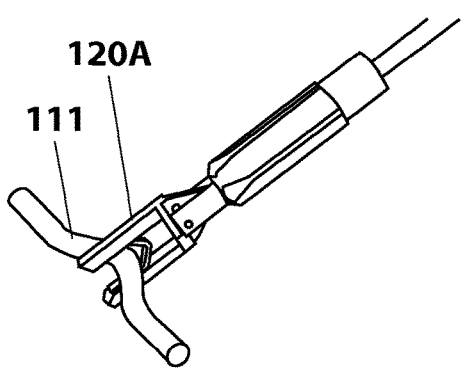
FIG. 25B depicts a perspective view of the clip applier of FIG. 25A substantially surrounding a target location, according to an exemplary embodiment of the surgical system.
Figure 25C:
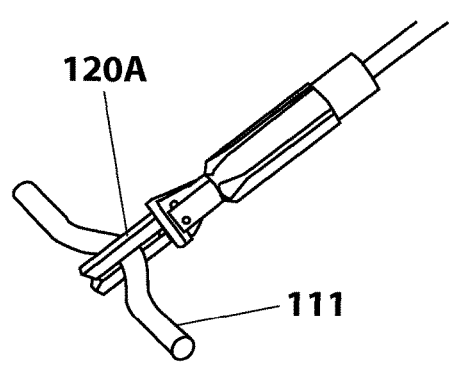
FIG. 25C depicts a perspective view of the clip applier of FIG. 25A applying a clip to a target location, according to an exemplary embodiment of the surgical system.
Figure 25D:
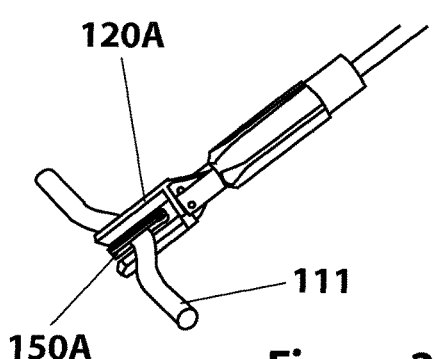
FIG. 25D depicts a perspective view of the clip applier of FIG. 25A opening the applier jaws and leaving the applied clip, according to an exemplary embodiment of the surgical system.
Figure 25E:
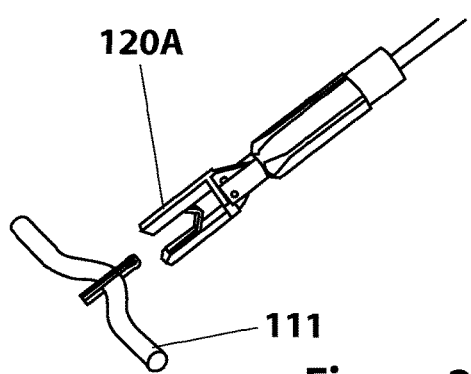
FIG. 25E depicts a perspective view of the clip applier of FIG. 25A withdrawing from the affixed clip, according to an exemplary embodiment of the surgical system.

FIG. 24A depicts an embodiment of a grasper 104 that can hold a set of clips 150A on its proximal portion for retrieval by a second surgical device 100A having a clip applier 120A. This grasper 104 can be one that is used for another aspect of the procedure such as retracting the liver in a gallbladder removal procedure. FIG. 24B24E depict the clip applier end effector 100A that has already been engaged to its control shaft going from its starting "closed" position to "open" and picking up a clip 150A from the proximal portion of the first grasper 104.

FIGS. 25A-25E depict the clip applier end effector 120A in use on a vessel 111 show the clip applier 120A approaching a clip site 119 such as a vessel 111, closing and deforming the metal clip 150A around the vessel 111 to seal it and leaving it behind. This process can then be repeated to use the rest of the clips on the first grasper 104, as described herein in reference to FIGS. 24A-E.

Figure 26A:
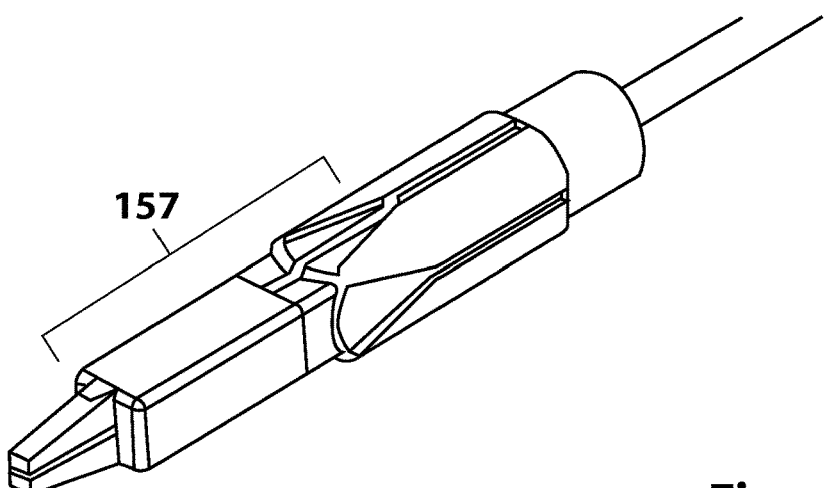
FIG. 26A shows an exterior perspective view of the surgical device comprising a single use, reloadable clip applier, according to one embodiment.
Figure 26B:
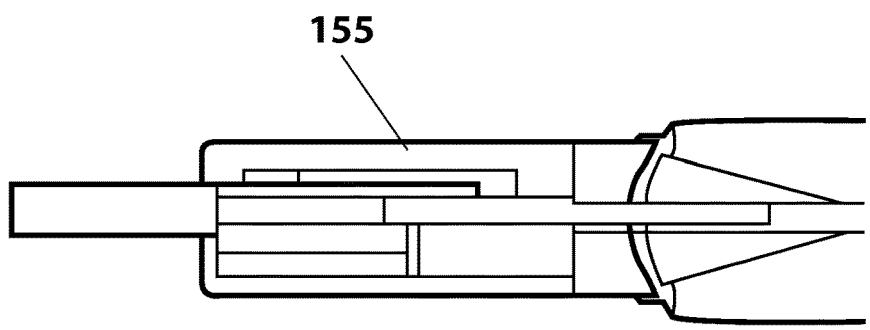
FIG. 26B shows an interior top-view view of the surgical device comprising a single use, reloadable clip applier, according to one embodiment.
Figure 26C:
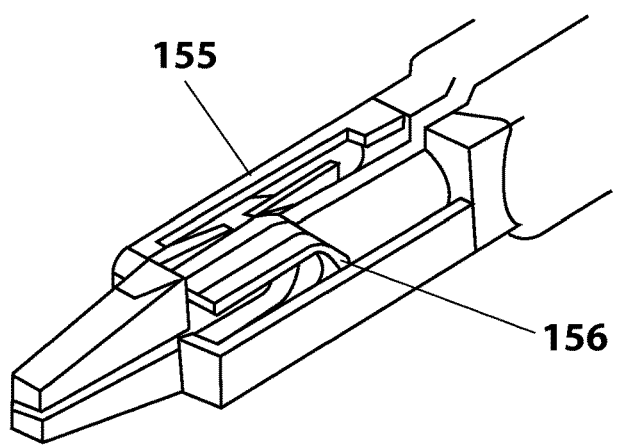
FIG. 26C shows an interior perspective view of the surgical device comprising a single use, reloadable clip applier, according to the embodiment of FIG. 26A.

FIGS. 26A-27G depict an exemplary implementation of the surgical device having a reloadable clip design 155. This embodiment uses a limited number of clips in a side-by-side configuration 156 to conserve overall end effector length 157 because size is more constrained with a modular design, as is shown in FIG. 26A.

FIGS. 26B-29D depict various implementations of the clip applier 155 opening, advancing the clip 150, closing (and deforming the clip (FIG. 27D) around the clip site 111A, leaving the clip behind and advancing the next clip to the "ready position." This process can then be repeated for the number of clips 150 in the device.

Figure 28A:
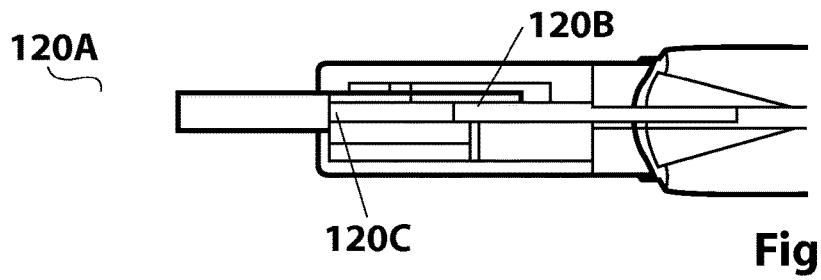
FIG. 28A depicts an interior top-view of an exemplary embodiment of the system comprising a single use, reloadable clip applier in the closed position.
Figure 28B:
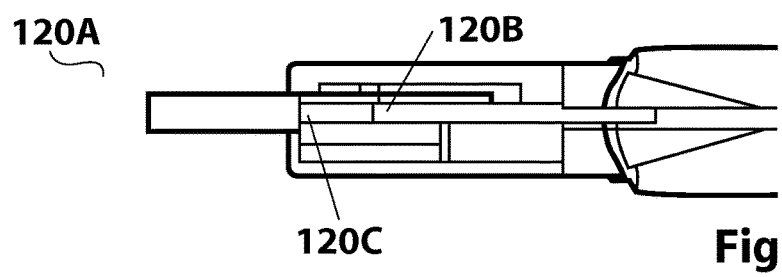
FIG. 28B depicts an interior top-view of an exemplary embodiment of the system comprising a single use, reloadable clip applier wherein the advancement slide is moving forward.
Figure 28C:
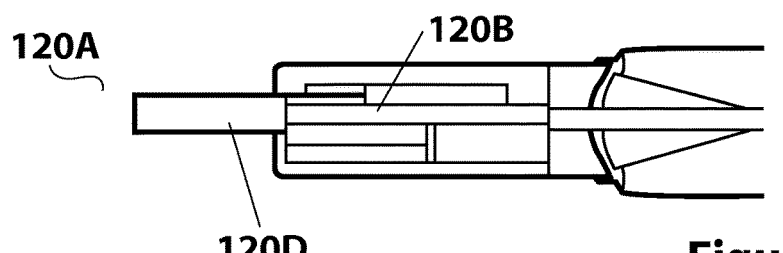
FIG. 28C depicts an interior top-view of an exemplary embodiment of the system comprising a single use, reloadable clip applier wherein the clip has reached the distal end of the jaws.
Figure 28D:
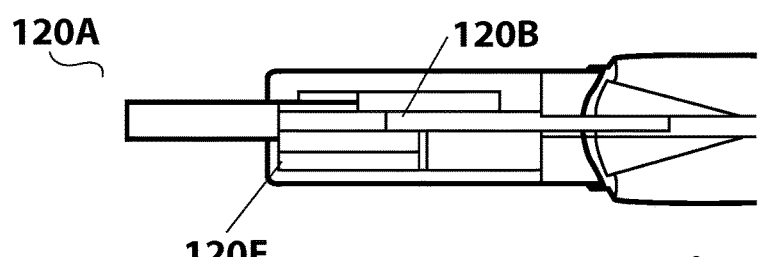
FIG. 28D depicts an interior top-view of an exemplary embodiment of the system comprising a single use, reloadable clip applier wherein the advancement slide has begun to retract.
Figure 28E:
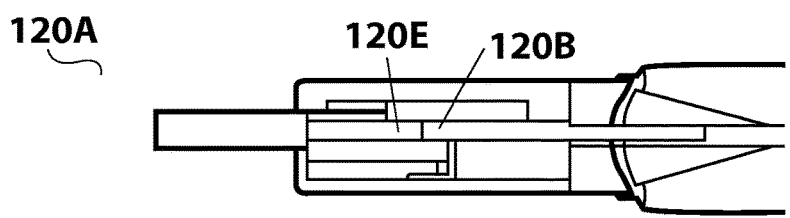
FIG. 28E depicts an interior top-view of an exemplary embodiment of the system comprising a single use, reloadable clip applier during reloading of a subsequent clip.
Figure 29A:
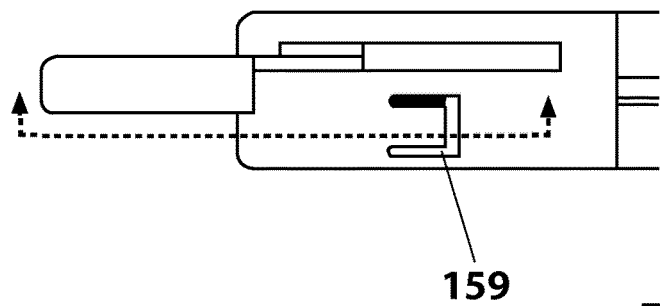
FIG. 29A depicts a top view of a of an exemplary embodiment of the system comprising a single use, reloadable clip applier further comprising clip tabs, wherein the jaws are open.
Figure 29B:
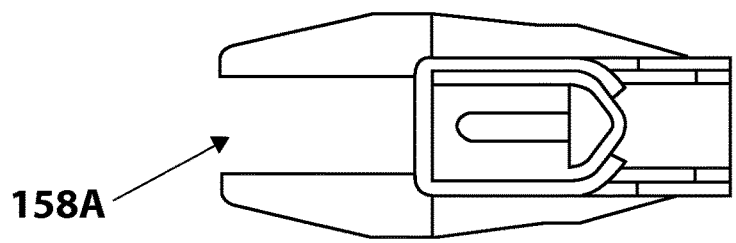
FIG. 29B is a side-view of the embodiment of FIG. 29B, wherein the jaws are open.
Figure 29C:
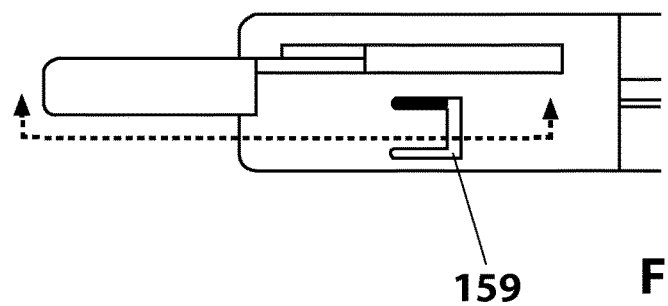
FIG. 29C depicts a top view of a of an exemplary embodiment of the system comprising a single use, reloadable clip applier further comprising clip tabs, wherein the jaws are closed.
Figure 29D:
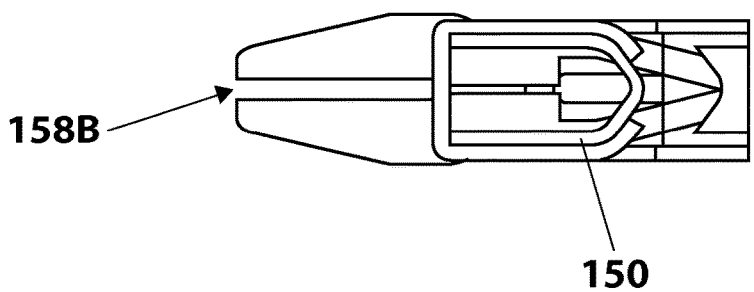
FIG. 29D is a side-view of the embodiment of FIG. 29B, wherein the jaws are closed.

FIG. 28A-28E show a partial section view of the clip advancement process where after the clip has been closed around the desired site and left behind, the next clip advances into the usage position when the handle is fully opened, as depicted in FIG. 28E.

Figure 27A:
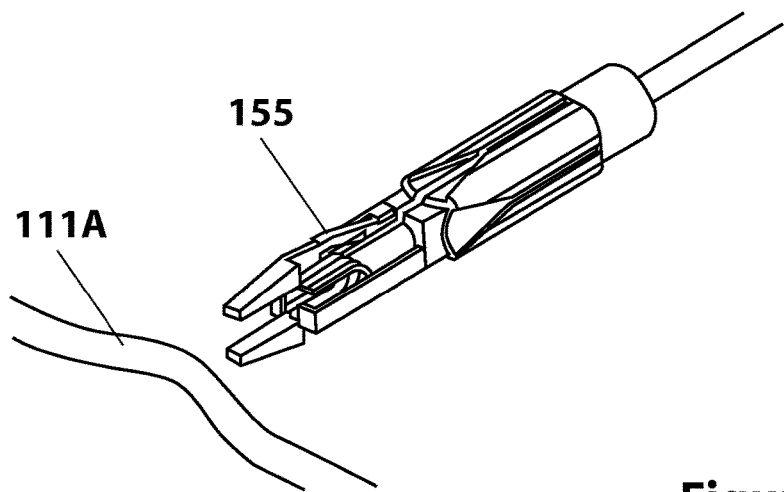
FIG. 27A depicts a perspective view of the surgical device comprising a single use, reloadable clip applier approaching a target location, according to an exemplary embodiment of the surgical system.
Figure 27B:
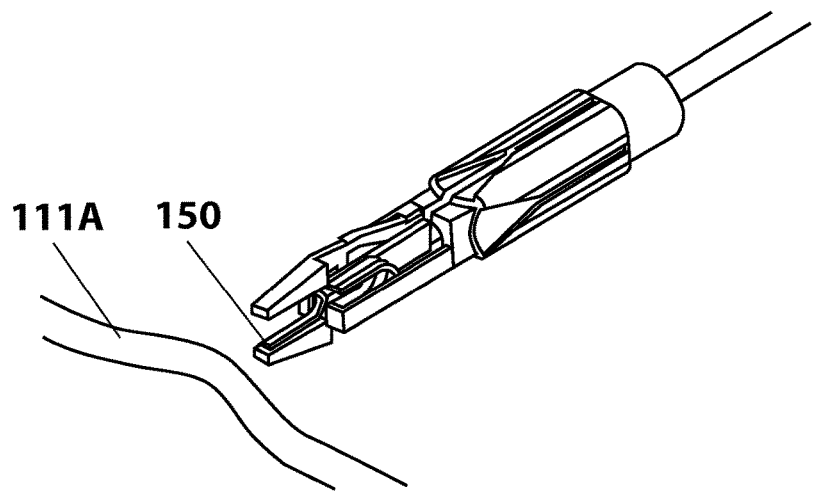
FIG. 27B depicts a perspective view of the clip applier of FIG. 27A loading a clip into the jaws, according to an exemplary embodiment.
Figure 27C:
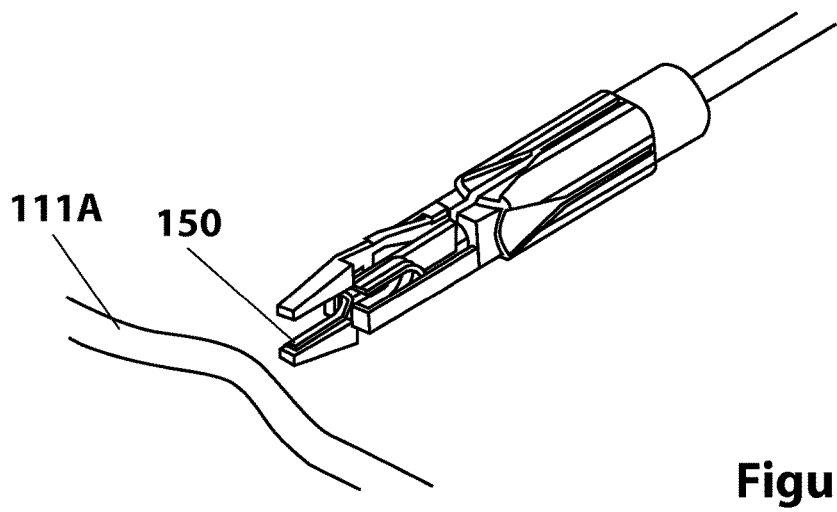
FIG. 27C depicts a perspective view of the clip applier of FIG. 27A loading a clip into the jaws, according to an exemplary embodiment.
Figure 27D:
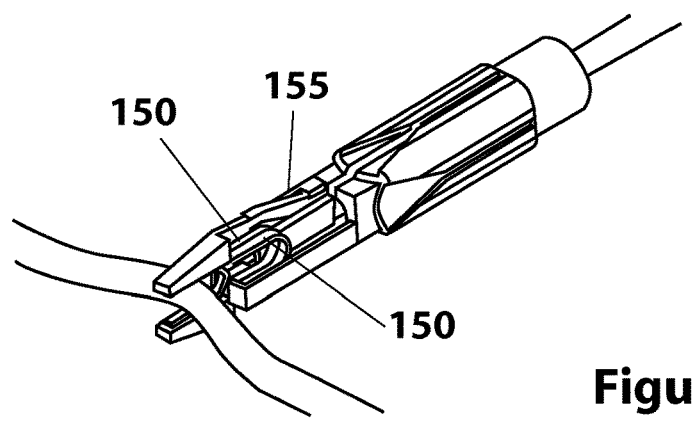
FIG. 27D depicts a perspective view of the clip applier of FIG. 27A closing/deforming a clip at a clip site, according to an exemplary embodiment.
Figure 27E:
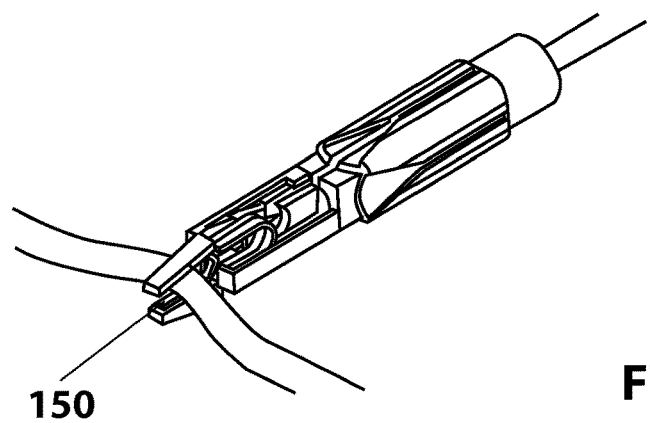
FIG. 27E depicts a perspective view of the clip applier of FIG. 27A applying a clip to a target location, according to an exemplary embodiment of the surgical system.
Figure 27F:
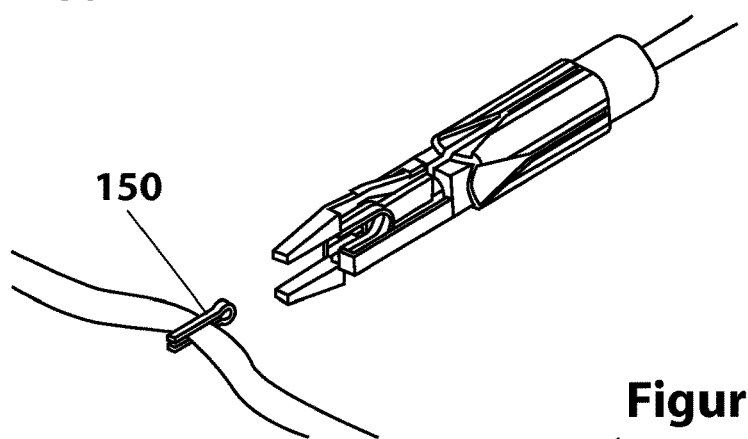
FIG. 27F depicts a perspective view of the clip applier of FIG. 27A opening the applier jaws and leaving the applied clip, according to an exemplary embodiment of the surgical system.
Figure 27G:
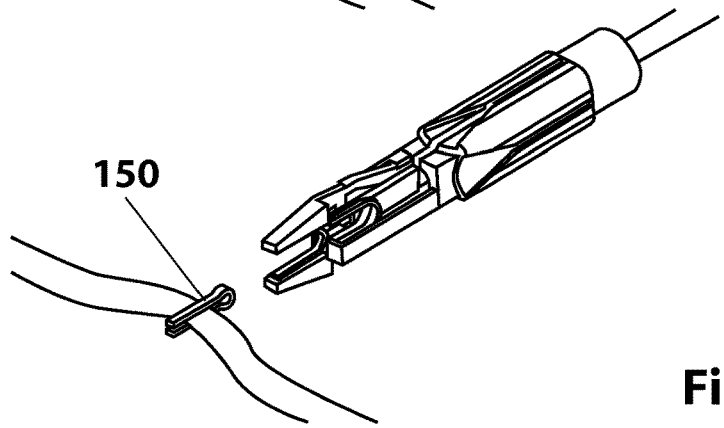
FIG. 27G depicts a perspective view of the clip applier of FIG. 27A withdrawing from the affixed clip and reloading the jaws, according to an exemplary embodiment of the surgical system.

FIG. 28A depicts an exemplary embodiment of the clip applier end effector 120A in the closed position. The closed position can be the initial introduction closed position or the closed position achieved after placing a clip. In these embodiments, when a user begins to open the handle the advancement slide 120B begins to move forward (FIG. 28B), thereby advancing the clip 120C distally, in the direction of the now open jaws. The advancement slide pushes the clip forward until the clip reaches the end of the jaws 120D (as depicted in FIGS. 27A and 28C). Once the user begins to close the handle the advancement slide begins to retract (as shown in FIG. 28D). When the advancement slide is fully retracted, the next clip 120E is free to shift to the side and seat into the advancement slide (as shown in FIG. 28E).

FIGS. 29A-29D depict various views of exemplary embodiments of the surgical device further comprising formed or machined tabs 159 to keep the deformable clips 150 in place when actuating the link and the clip advancer is moved proximally to close the jaws 158A, 158B.

Figure 30A:
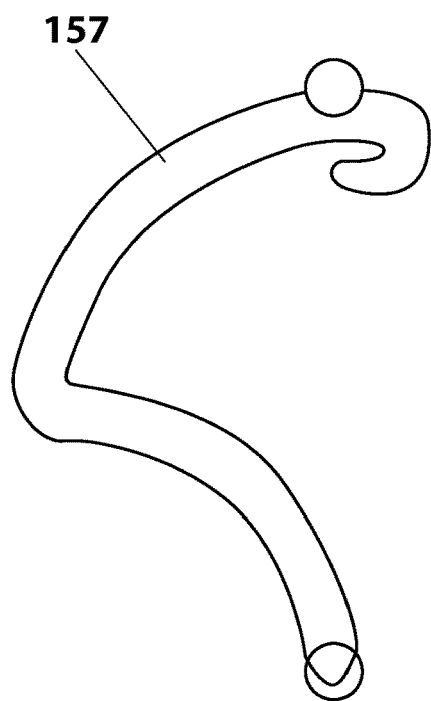
FIG. 30A is a side-view of an exemplary embodiment of a Hemo-Lock clip.
Figure 30B:
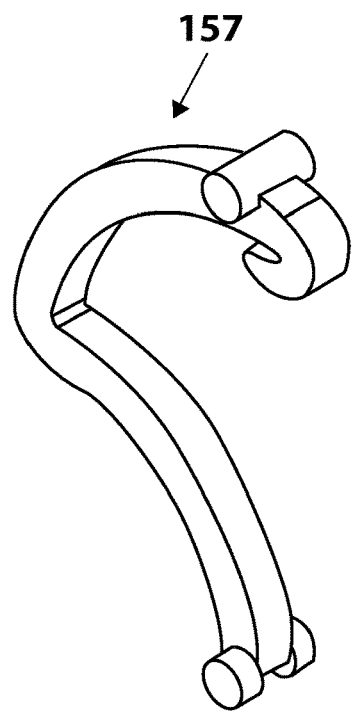
FIG. 30B is a perspective view of a Hemo-Lock clip.

FIG. 30A-32D depict various embodiments of the surgical device capable of using Hemo-Lock style clips 157. FIGS. 30A-30B show exemplary embodiments of the Hemo-Lock style clips, which are commercially available. In certain embodiments of the surgical device and system, the clip adaptor jaws 120 can be adapted to accommodate the Hemo-Lock style clips 157. Certain procedures are ideally suited for medical clips that are made from an elastic material that "locks" 157A closed rather than being "crushed" or permanently deformed by the device. One example of this style of clip is the "Hemo-Lock" clip. Implementations of the surgical depicted in FIGS. 31A-32D are adapted to accommodate this style of clip 157.

Figure 31A:
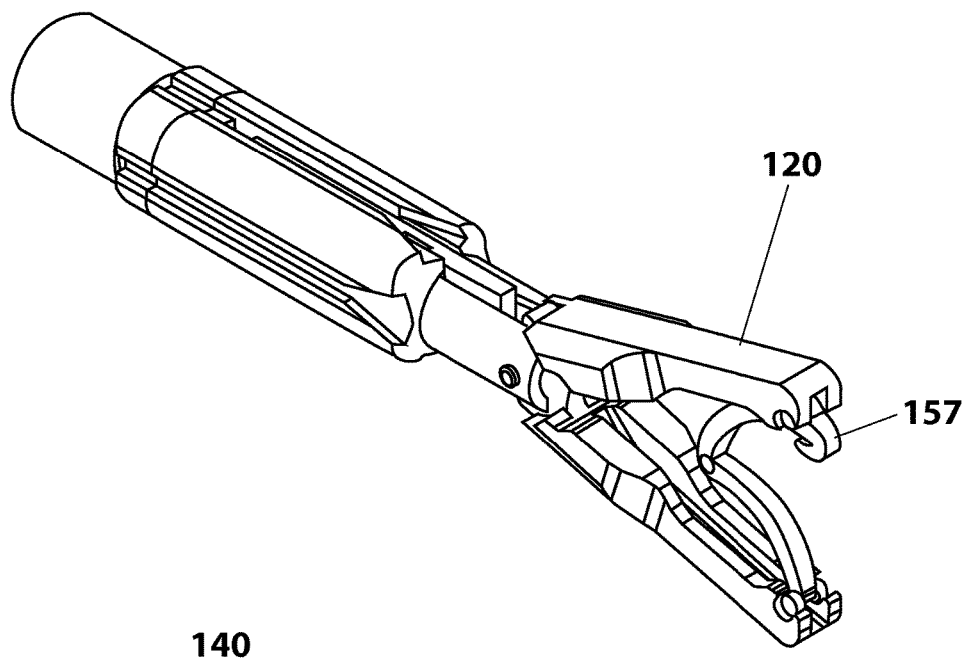
FIG. 31A is a perspective view of one embodiment of a clip applier end effector with open jaws and comprising an open Hemo-Lock clip.

FIG. 31A depicts a Hemo-Lock Clip 157 being inserted into the end effector wherein the jaws 120 are in the open position, and the locking ring 140 is in an locked position.

Figure 31B:
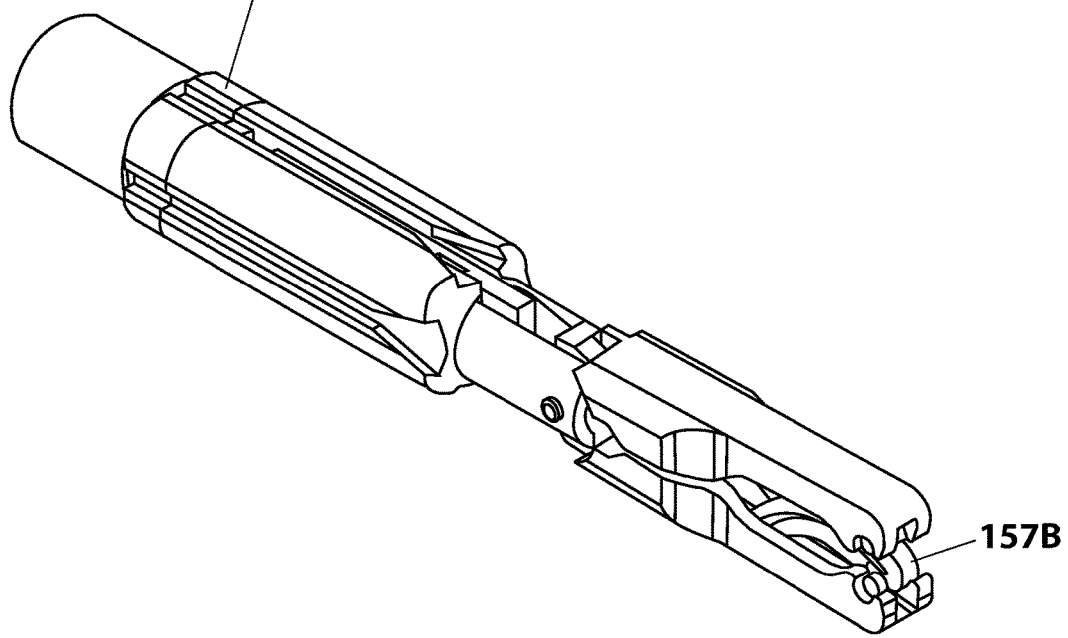
FIG. 31B is a perspective view of one embodiment of a clip applier end effector with substantially closed jaws and comprising an unlocked Hemo-Lock clip.

In the embodiment of FIG. 31B, the jaws 120 are closed such that the clip is substantially, but not completely closed 157B, and therefore capable of returning to the open position if released. In certain embodiments, this closure can be either external or internal, for example if the end effector is attached to a cannular shaft. In certain implementations, this also coincides with the alignment position previously described in relation to FIGS. 16A-16D.

Figure 31C:
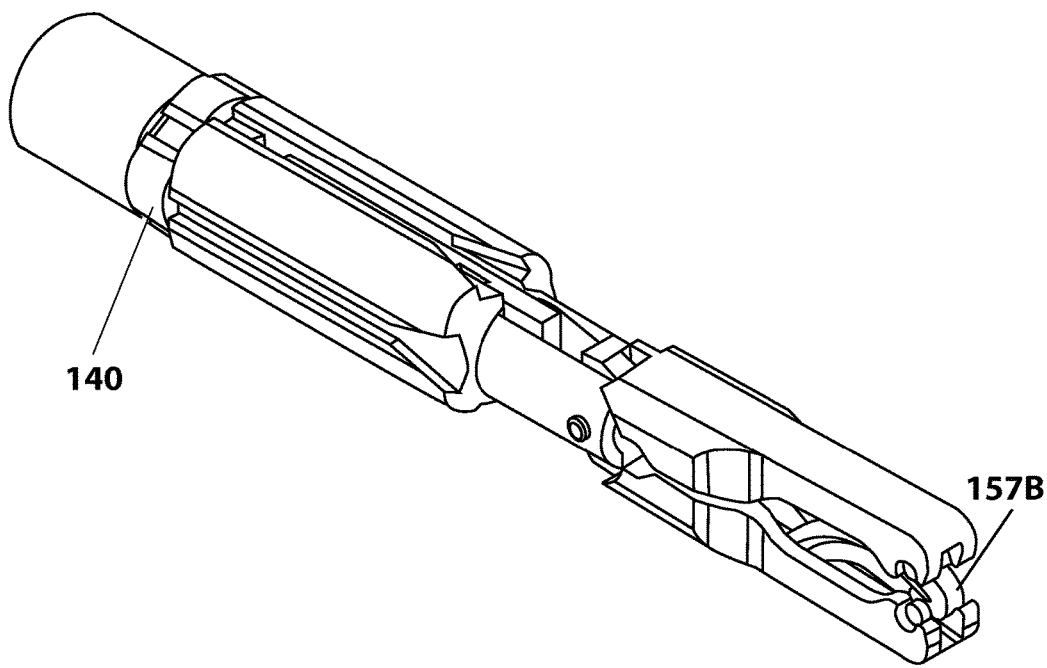
FIG. 31C is a perspective view of one embodiment of a clip applier end effector with substantially closed jaws and comprising an unlocked Hemo-Lock clip wherein the locking ring has been engaged.

FIG. 31C further depicts an embodiment wherein the toolhead is inserted into the patient with the jaws 120 in the substantially closed state 157B described above into an introduction device (as described in relation to FIGS. 19A-23F, for example). In the embodiments, the locking ring 140 is rotated as is shown into the locked position. In these implementations, the jaws 120 are thus now locked in the substantially but not completely closed position 157B due to the internal actuating link interacting with the locking ring 140, as described elsewhere herein. As such, the toolhead and jaws 120 are now ready to be introduced into the operation field.

Figure 31D:
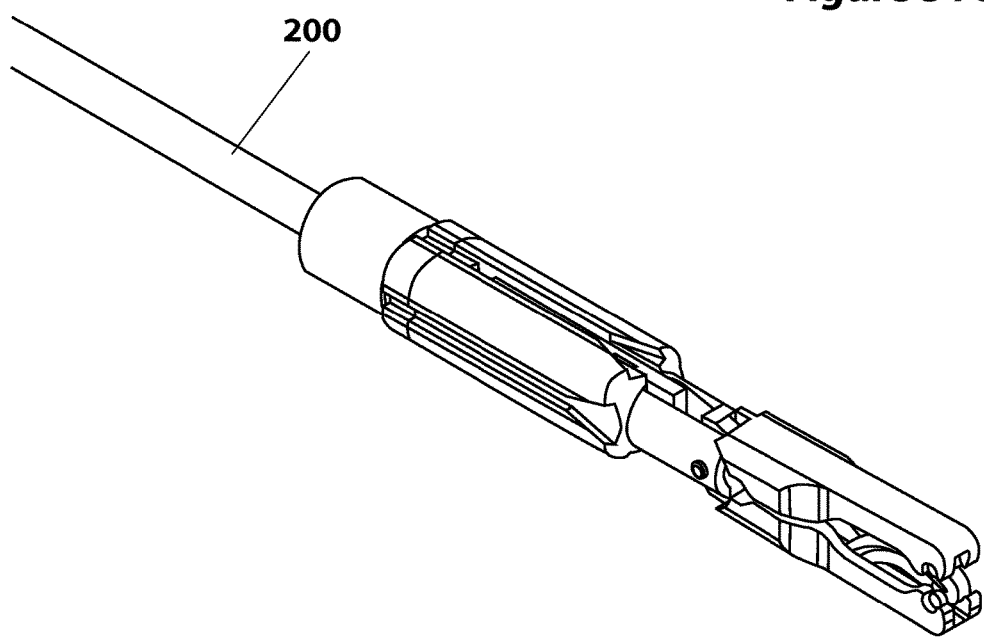
FIG. 31D is a perspective view of the embodiment of FIG. 31C, wherein a cannula has been inserted into the end effector.

FIG. 31D depicts a cannular shaft 200 which can then be inserted to unlock the toolhead from the introducer. The toolhead is now locked to the cannular shaft and the jaws have now been unlocked and are correspondingly ready to be opened so as to correspondingly open the Hemo-Lock clip 157 for use.

Figure 32A:
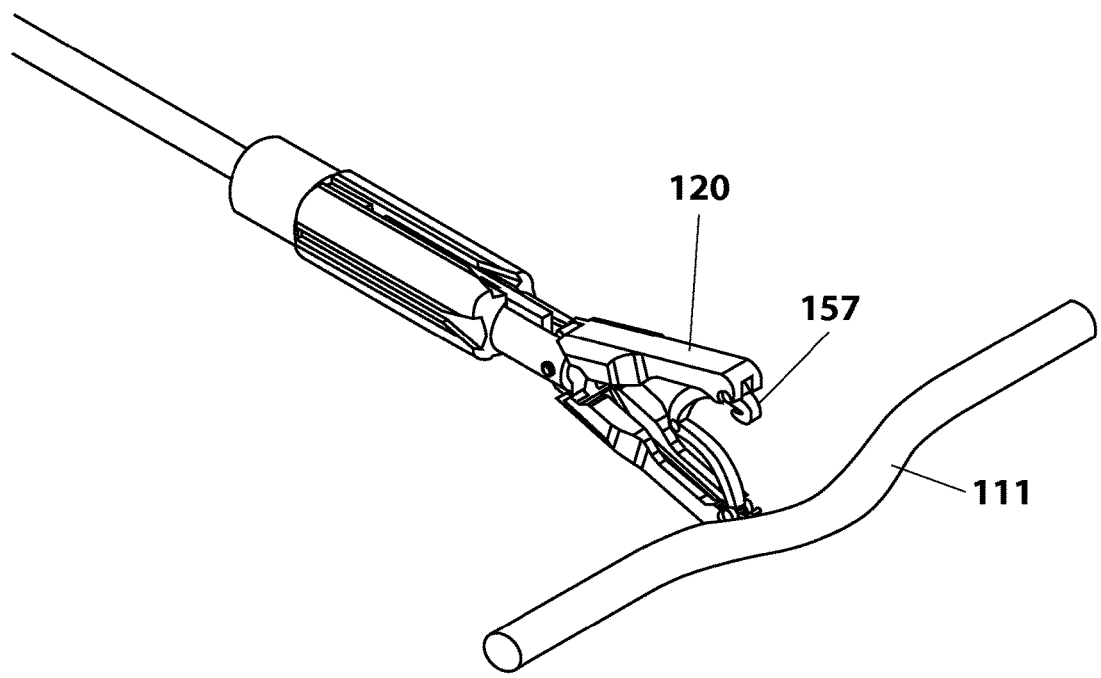
FIG. 32A is a perspective view of the embodiment of one embodiment of a clip applier end effector with open jaws and comprising an open Hemo-Lock clip approaching a target site.
Figure 32B:
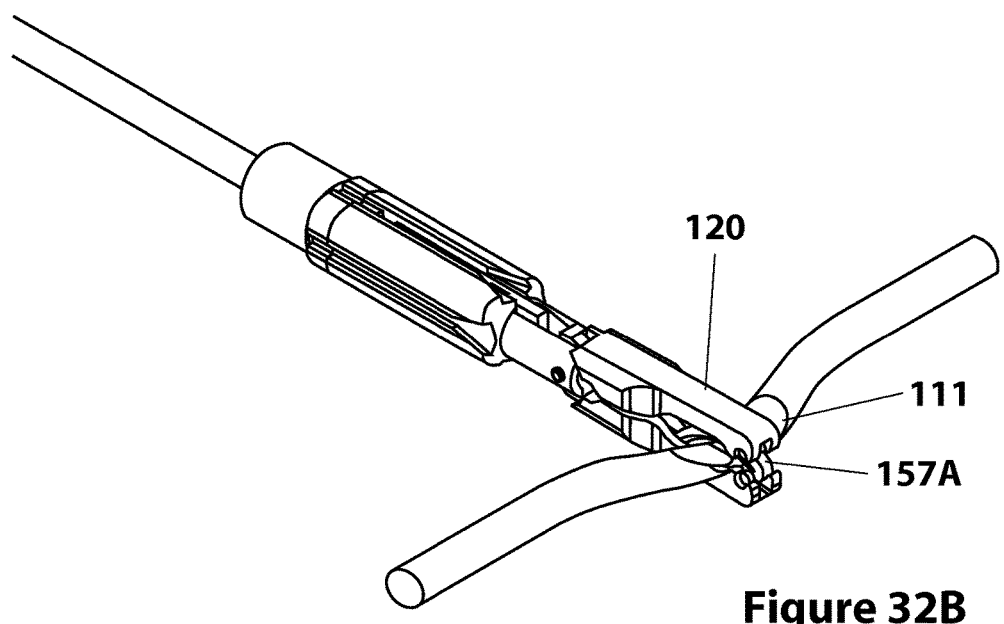
FIG. 32B is a perspective view of one embodiment of a clip applier end effector with substantially closed jaws around the target site and comprising and locked Hemo-Lock clip on the target site.

FIGS. 32A-32D depicts an embodiment in which the toggle switch on the handleset (not shown, but described in relation to FIGS. 4A-4B and 12*a*-15B) is first placed in the "up" position allowing the handle, and thus the jaws 120 and Hemo-Lock clip 157, to be opened for ready application to the vessel 111 (FIG. 32A). In the embodiment of FIG. 32B, the open jaws 120 can then be placed over the target clip site 111 and the action of the handleset may be activated so as to lock the Hemo-Lock clip 157A. In certain embodiments, the action of the handleset being closed fully closes the jaws as to lock the Hemo-Lock clip in the closed position. In these embodiments, as the toggle switch on the handle is in the "up" position the handle and thus the jaws are permitted to go past the alignment position into the overthrow position. This fully closes the clip, activating it 157A.

Figure 32C:
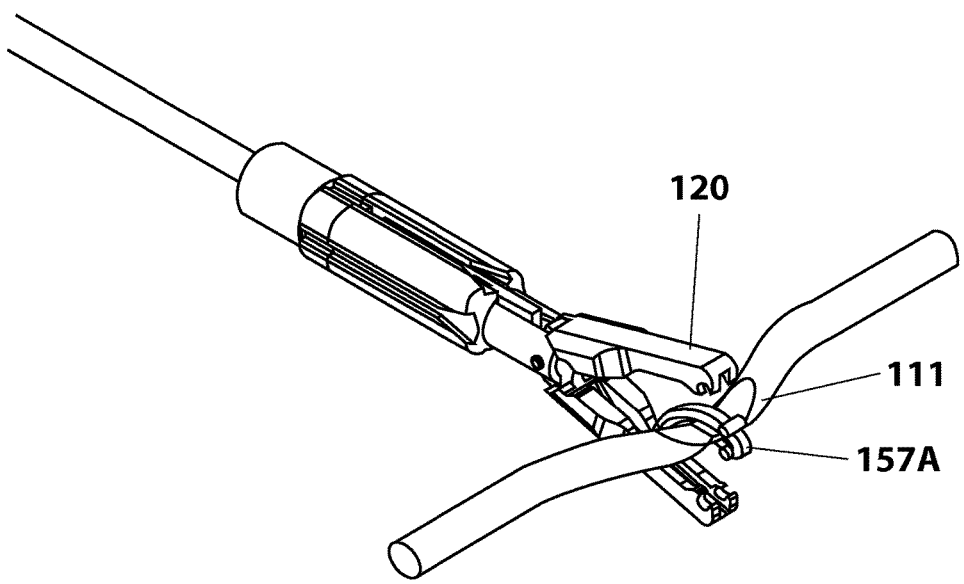
FIG. 32C is a perspective view of the end effector of FIG. 32B, wherein the jaws have opened and the Hemo-Lock clip remains locked on the target site.
Figure 32D:
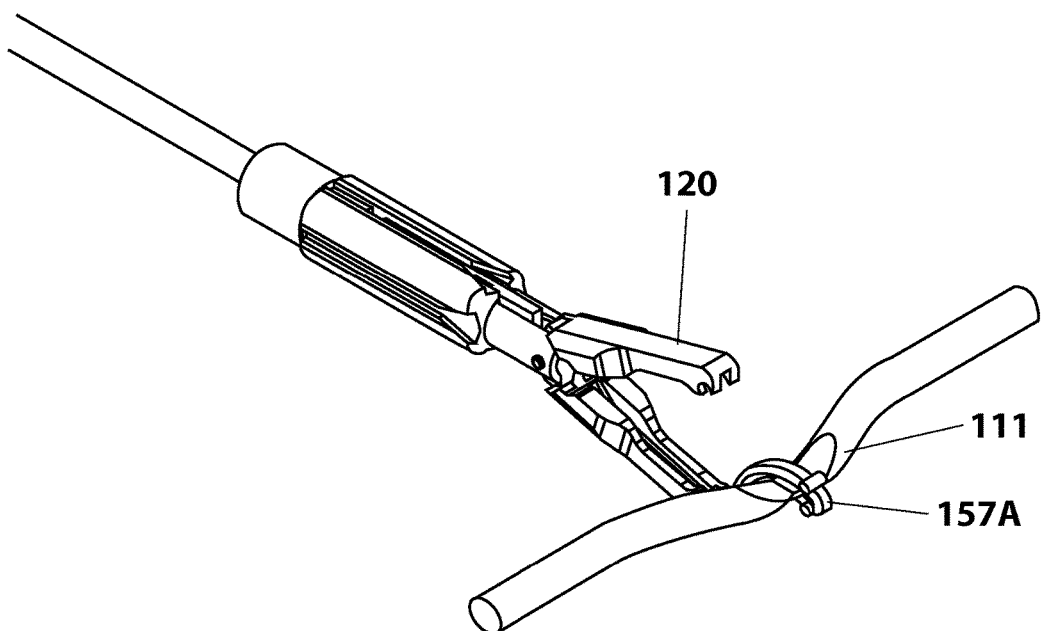
FIG. 32D is a perspective view of the embodiment of FIG. 32C, wherein the end effector is being retracted from the target site.

As shown in FIGS. 32C-D, because the clip was fully closed 157A and activated it will remain closed when the jaws 120 are opened again, thus allowing the jaws 120 and toolhead to be retracted.

Some implementations of the surgical device feature a compliant cannula rotation knob. One issue observed in user testing results from users trying to force the rotation of the outer cannula shaft when the components are not properly aligned. This can damage some of the components without users knowing they are using the device incorrectly. Additionally, even if all of the components are properly aligned, users can attempt to over rotate the cannula shaft, leading to damage as well. To prevent both of these issues, we can create compliance between the knob users interact with and the outer cannula shaft that is engaging the end effector. To prevent damage to these components, the stiffness of the link between the knob and the cannula shaft is significantly less than the stiffness of the components in the end effector assembly. The difference in stiffness means that if a user tries to apply too much force, the knob will feel differently when a user is trying to rotate it when the components are misaligned or the lock is already fully rotated. This difference in feel can be honed to make it a useful feedback tool for the user.

In further embodiments, the compliant cannula can be combined or replaced with a clutch that prevents a user from applying a rotational force that could damage the components in the end effector assembly. This clutch action could be accompanied with an audible and tactile click to convey that the force a user is applying is excessive.

During use, the abdomen can be inflated with carbon dioxide to allow the surgeon more room to work with and maneuver laparoscopic tools. The control shaft can be 14 gauge. The control shaft can penetrate the skin of the abdomen, for example, leaving no scar (e.g., 14 gauge needles are considered to not leave a scar).

A rotating grasper or introducer rod with a rotating connection to the introducer can be used to handle, maneuver and deliver the tool into the abdominal cavity. The surgeon can use a drawstring to tighten or loosen the grasper, as well as an actuating mechanism to rotate the grasper.

The introducer rod and the tool can be inserted through a first access site at the umbilicus. The surgeon can use an endoscope to locate the end of the control shaft 12 within the abdomen and attach the tool to the control shaft.

The control shaft can have two slits configured to allow a tool to attach to the distal end of the control shaft. The tool can have spring-like locks that can insert into the two slits of the control shaft. The tool can be attached to the control shaft in the abdominal cavity.

Once the tool is attached to the control shaft, the surgeon can use the control shaft and the tool as a laparoscopic tool. The control shaft can have an actuating rod (e.g., the inner sub-shaft) that can actuate the tool. For example, the actuating rod can slide a rack-and-pinion mechanism to open and close a grasper tool. The grasper tool can be spring-loaded so the inner sub-shaft can close the grasper when actuated.

Once the surgeon is finished with the tool, the surgeon can activate a sleeve within a needle that can release the spring locks from the slits on the control shaft. A rotation grasper can then remove the tool through the first access site.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

While the retraction systems, in accordance with the present disclosure, have been described as being used in connection with surgical procedures performed within the abdominal cavity, it is envisioned that the retraction systems disclosed may be used in other surgical procedures. It is understood that various modifications may be made to the embodiments of the presently disclosed surgical device and system. Therefore, the above description should not be construed as limiting, but merely illustrative of the variations described herein.

What is claimed is:

1. A medical introduction system, the system comprising:
   (a) an elongate trocar tube defining a trocar lumen;
   (b) a laparoscope comprising:
      (i) an elongate laparoscope rod comprising distal and proximal ends;
      (ii) a camera positioned at a proximal end of the elongate rod and further comprising a lens at the distal end of the laparoscope rod; and
   (c) an introduction component configured to be positioned through the trocar lumen, the introduction component comprising:
      (i) an elongate introduction tube;
      (ii) an end effector operably coupleable to a distal end of the introduction tube;
      (iii) a distal receiving slot defined at a distal portion of the introduction tube;
      (iv) a proximal receiving slot defined at a proximal portion of the introduction tube; and
      (v) an adjustable locking mechanism operationally integrated with the introduction component and laparoscope, wherein the distal receiving slot and proximal receiving slot are configured to allow the laparoscope rod to be selectively oriented and locked at both coaxial and deflected positions relative to the longitudinal axis of the introduction tube,
   wherein the introduction component is configured to allow the introduction component and laparoscope to be introduced through the trocar lumen simultaneously,
   wherein the elongate laparoscope rod is deflectable in relation to a longitudinal axis of the elongate introduction tube.

2. The medical introduction system of claim 1, wherein the proximal receiving slot is disposed at substantially 180 degrees around the longitudinal axis of the introduction tube in relation to the distal receiving slot.

3. The medical introduction system of claim 1, wherein the laparoscope rod and camera are independently rotatable relative to one another by way of a proximal operation handle.

4. The medical introduction system of claim 3, further comprising a rotation guide configured to regulate rotation of the laparoscope rod relative to the camera.

5. The medical introduction system of claim 1 further comprising a handle tool comprising:
   (a) a control shaft operably coupleable with the end effector; and
   (b) a handleset comprising:
      (i) a proximal handle;
      (ii) a distal handle;
      (iii) a locking slide;
      (iv) a rotation knob; and
      (v) a toggle switch,
   wherein the handleset is configured to be capable of a plurality of positions.

6. The medical introduction system of claim 5, wherein the end effector is configured to be able to be engaged by the handle tool.

7. The medical introduction system of claim 6, wherein the end effector further comprises a cannula guide cap.

8. The medical introduction system of claim 7, further comprising a visual indicator.

9. The medical introduction system of claim 1, wherein the end effector is a clip applier.

10. The medical introduction system of claim 9, wherein the clip applier further comprises a plurality of clips.

11. The medical introduction system of claim 1, wherein the end effector is a grasper.

12. The medical introduction system of claim 11, wherein the grasper further comprises a plurality of clips affixed at the proximal portion of the end effector.

13. The medical introduction system of claim 1, wherein the end effector is a hemo-lock clip applier.

14. A medical introduction system, the system comprising:
   (a) an elongate trocar tube defining a trocar lumen;
   (b) a laparoscope comprising:
      (i) an elongate laparoscope rod comprising distal and proximal ends;
      (ii) a camera positioned at a proximal end of the elongate rod and further comprising a lens at the distal end of the laparoscope rod, wherein the distal end of the laparoscope ends in a bezel;
   (c) an introduction component configured to be positioned through the trocar lumen, the introduction component comprising:
      (i) a camera attachment mechanism;
      (ii) an elongate introduction tube;
      (iii) a distal receiving slot defined at a distal portion of the introduction tube; and
      (iv) a proximal receiving slot defined at a proximal portion of the introduction tube and disposed at substantially 180 degrees around the longitudinal axis of the introduction tube in relation to the distal receiving slot,
   wherein the distal receiving slot and proximal receiving slot are configured to allow the laparoscope rod to be selectively oriented at both coaxial and deflected positions relative to a longitudinal axis of the introduction tube; and
   (d) an adjustable locking mechanism operationally integrated with the introduction component and laparoscope.

15. The medical introduction system of claim 14, further comprising a rotation mechanism, wherein the laparoscope rod and camera are independently rotatable relative to one another by way of a proximal operation handle.

16. The medical introduction system of claim 15 further comprising a handle tool comprising:
   (a) a control shaft operably coupleable with an end effector; and
   (b) a handleset comprising:
      (i) a proximal handle;
      (ii) a distal handle;
      (iii) a locking slide;
      (iv) a rotation knob; and
      (v) a toggle switch,
   wherein the handleset is capable of a plurality of operational positions.

17. A medical introduction system, the system comprising:
(a) an elongate trocar tube defining a trocar lumen;
(b) a laparoscope comprising:
  (i) an elongate laparoscope rod comprising distal and proximal ends;
  (ii) a camera positioned at the proximal end of the laparoscope rod;
  (iii) a lens positioned at the distal end of the laparoscope rod; and
  (iv) a bezel disposed at the distal end of the laparoscope rod; and
(c) an introduction component configured to be positioned through the trocar lumen, the introduction component comprising:
  (i) an elongate introduction tube;
  (ii) a distal receiving slot defined at a distal portion of the introduction tube;
  (iii) a proximal receiving slot defined at a proximal portion of the introduction tube, wherein the distal receiving slot and proximal receiving slot are configured to allow the laparoscope rod to be selectively oriented at both coaxial and angularly deviated positions relative to a longitudinal axis of the introduction tube;
  (iv) an adjustable locking mechanism operationally integrated with the introduction component and laparoscope, wherein the adjustable locking mechanism is configured to lock the laparoscope rod in the coaxial and angularly deviated positions; and
  (v) a rotation mechanism, wherein the laparoscope rod and camera are independently rotatable relative to one another by way of a proximal operation handle.

18. The medical introduction system of claim 17, wherein the proximal receiving slot is disposed at substantially 180 degrees around the longitudinal axis of the introduction tube in relation to the distal receiving slot.

19. The medical introduction system of claim 17, further comprising a handle tool comprising:
(a) a control shaft operably coupleable with an end effector operably coupleable to a distal end of the introduction tube; and
(b) a handleset,
wherein the handleset is capable of a plurality of operational positions.

20. The medical introduction system of claim 17, further comprising an end effector operably coupleable to a distal end of the introduction tube, wherein the end effector is a clip applier, a grasper, or a hemo-lock clip applier.

* * * * *